United States Patent
Morariu

(10) Patent No.: US 7,666,442 B2
(45) Date of Patent: Feb. 23, 2010

(54) TOPICAL COMPOSITIONS COMPRISING BENFOTIAMINE AND PYRIDOXAMINE

(75) Inventor: Marius Morariu, Brooklyn, NY (US)

(73) Assignee: Tracie Martyn International, LLC, New York, NY (US)

( * ) Notice: Subject to any disclaimer, the term of this patent is extended or adjusted under 35 U.S.C. 154(b) by 517 days.

(21) Appl. No.: 11/218,226

(22) Filed: Aug. 31, 2005

(65) Prior Publication Data

US 2006/0045896 A1 Mar. 2, 2006

Related U.S. Application Data

(60) Provisional application No. 60/605,750, filed on Aug. 31, 2004.

(51) Int. Cl.
*A61K 31/51* (2006.01)
*C07D 213/00* (2006.01)
(52) U.S. Cl. .................. 424/401; 546/300; 544/543
(58) Field of Classification Search .............. 424/401; 546/300; 544/543
See application file for complete search history.

(56) References Cited

U.S. PATENT DOCUMENTS

| | | | |
|---|---|---|---|
| 3,819,480 A | 6/1974 | Hochshild | |
| 5,443,834 A | 8/1995 | Aki et al. | |
| 5,723,502 A * | 3/1998 | Proctor | 514/741 |
| 5,869,672 A * | 2/1999 | Kozikowski et al. | 546/156 |
| 6,011,067 A | 1/2000 | Hersh | |
| 6,083,529 A * | 7/2000 | Manzo et al. | 424/450 |
| 6,093,404 A * | 7/2000 | Kattan | 424/732 |
| 6,165,500 A | 12/2000 | Cevc | |
| 6,261,598 B1 * | 7/2001 | Runge et al. | 424/456 |
| 6,310,092 B1 * | 10/2001 | Kelleher et al. | 514/471 |
| 6,447,820 B1 * | 9/2002 | Niazi | 424/767 |
| 6,455,589 B1 | 9/2002 | Ames et al. | |
| 6,465,421 B1 * | 10/2002 | Duranton et al. | 514/1 |
| 6,740,668 B1 | 5/2004 | Baynes et al. | |
| 6,750,209 B1 | 6/2004 | Hudson et al. | |
| 6,759,065 B1 | 7/2004 | Ruijten | |
| 6,783,754 B2 * | 8/2004 | Mankovitz | 424/59 |
| 2003/0165456 A1 * | 9/2003 | Duffy et al. | 424/74 |
| 2003/0190337 A1 | 10/2003 | Bissett | |
| 2004/0092482 A1 | 5/2004 | Gupta | |
| 2004/0122061 A1 | 6/2004 | Khalifah | |
| 2005/0019354 A1 | 1/2005 | Perricone | |

FOREIGN PATENT DOCUMENTS

WO  WO 02/13838 * 2/2002

OTHER PUBLICATIONS

U.S. Department of Health and Human Services—Food and Drug Administation—Center of Drug Evaluation and Research(CDER)—Center for Biologics Evaluation and Research(CBER), Guidance for Industry(Container Closure Systems for Packaging Human Drugs and Biologics), Chemistry, Manufacuring and Controls Documentation, May 1999.*
Fusaro, Ramon M. et al. 2005. The Maillard Reaction for Sunlight Protection. *Ann. N. Y. Acad. Sci.* 1043:174-183.
Haupt, E. et al. 2005 Benfotiamine in the treatment of diabetic polyneuropathy—a three-week randomized, controlled pilot study (BEDIP Study). *International Journal of Clinical Pharmacology and Therapeutics* 43(2)71-77.
Hartog, Jasper W.L. et al. 2005. Accumulation of Advanced Glycation End Products, Measured as Skin Autofluorescence, in Renal Disease. *Ann. N. Y. Acad. Sci.* 1043:299-307.
Pageon, Hervé and Daniel Asselineau. 2005. An in Vitro Approach to the Chronological Aging of Skin by Glycation of the Collagen. The Biological Effect of Glycation on the Reconstructed Skin Model. *Ann. N. Y. Acad. Sci.* 1043:529-532.
Voziyan, Paul A. and Billy G. Hudson. 2005. Pyridoxamine. The Many Virtues of a Maillard Reaction Inhibitor. *Ann. N. Y. Acad. Sci.* 1043:807-816.
Chumnantana, R. et al. 2004. Vitamin $B_6$ compounds prevent the death of yeast cells due to menadione, a reactive oxygen generator. *Biochimica et Biophysica Acta* 1722:84-91.
Menè, Paolo et al. 2003. Clinical Potential of Advanced Glycation End-Product Inhibitors in Diabetes Mellitus. *Am. J. Cardiovasc. Drugs* 3(5):315-320.
Vasan, Sara et al. 2003. Therapeutic potential of breakers of advanced glycation end product-protein crosslinks. *Archives of Biochemistry and Biophysics* 419:89-96.
Squier, Thomas C. 2001. Oxidative stress and protein aggregation during biological aging. *Experimental Gerontology* 36:1539-1550.
Verzijl, Nicole et al. Effect of Collagen Turnover on the Accumulation of Advanced Glycation End Products. *The Journal of Biological Chemistry* 275(50):39027-39031.
Price, David L. et al. 2001. Chelating Activity of Advanced Glycation End-product Inhibitors. *The Journal of Biological Chemistry* 276(52):48967-48972.
Khalifah, Raja G. et al. 1999. Amadorins: Novel Post-Amadori Inhibitors of Advanced Glycation Reactions. *Biochemical and Biophysical Research Communications* 257:251-258.
Woelk, H. et al. 1998. Benfotiamine in Treatment of Alcoholic Polyneuropathy: An 8-Week Randomized Controlled Study (BAP I Study). *Alcohol & Alcoholism* 33(6):631-638.
Stracke, H. et al. 1996. A Benfotiamine-vitamin B combination in treatment of diabetic polyneuropathy. *Exp. Clin. Endocrinol. Diabetes* 104:311-316.
PCT International Search Report for International Application No. PCT/US05/31144, dated Oct. 11, 2006.

* cited by examiner

*Primary Examiner*—Gina C Yu
(74) *Attorney, Agent, or Firm*—Darby & Darby; Lydia G. Olson

(57) ABSTRACT

The present invention provides a composition comprising an effective amount of benfotiamine and an effective amount of pyridoxamine in a suitable vehicle for topical application. The present compositions are useful in improving the appearance of aged skin characterized by wrinkles, loss of elasticity, and hyperpigmentation caused by chronoaging and/or photoaging of skin, by inhibiting particularly skin damage resulting from reactive carbonyl species (RCS), glycation of skin proteins, formation of advanced glycation endproducts (AGEs) and formation of advanced lipoxidation endproducts (ALEs).

15 Claims, No Drawings

TOPICAL COMPOSITIONS COMPRISING BENFOTIAMINE AND PYRIDOXAMINE

This application claims priority to provisional application No. 60/605,750 filed Aug. 31, 2004, herein incorporated by reference.

FIELD OF INVENTION

The present invention relates to the topical application of compositions containing benfotiamine and pyridoxamine for the prevention and/or treatment of damage to skin, particularly skin damage resulting from reactive carbonyl species (RCS), glycation of skin proteins, formation of advanced glycation endproducts (AGEs) and formation of advanced lipoxidation endproducts (ALEs).

BACKGROUND OF THE INVENTION

Skin is subject to abuse by many extrinsic (environmental) factors as well as intrinsic factors. A common extrinsic factor is exposure to ultraviolet radiation. Whether extrinsic or intrinsic, the abuse results in skin aging. Skin aging happens in two ways: (1) through the natural aging process which dermatologists call chronological aging (also known as chronoaging); and (2) through UV rays in sunlight accelerating the aging process which dermatologists call photoaging. Chronoaging results in thinning, loss of elasticity and general degradation of skin. As the skin naturally ages, there is a reduction in the cells and blood vessels that supply the skin. There is also a flattening of the dermal-epidermal junction which results in weaker mechanical resistance. As a consequence, older persons are more susceptive to blister formation in cases of mechanical traumas or disease processes (Oikarinen et al., *Photodermatal. Photoimmunol. Photomed.*, 7:3-4 (1990)).

By contrast photoaging, or premature aging, is a process in which the skin changes in appearance as a result of repeated exposure to sunlight. Typically, photoaging occurs in areas of habitual exposure, such as the scalp, face, ears, neck, chest, forearms and hands. The changes associated with photoaging include elastosis, atrophy, wrinkling, vascular changes (diffuse erythema, ecchymoses, and telangiectasias), pigmentary changes (lentigines, freckles, and areas of hypo- and hyper-pigmentation), and the development of seborrheic keratosis, actinic keratosis, comedones and cysts.

Decreased elasticity of the cardiovascular system is one of the hallmarks of the normal aging process of mammals and has been linked to an age-related accumulation of advanced glycation endproducts (AGEs). Glycation is the product of reaction between a sugar and the free amino group of proteins and involves cross-linking. The linking of glycosylation byproducts to proteins results in the development of large, cross-linked molecules that inhibit the ability of the cell to function normally, thereby increasing the aging process. In addition, AGEs in tissues increase the rate of free radical production to 50-times the rate of free-radical production by unglycated proteins, even further increasing the rate of the aging process.

The relationship between sugar and the aging process is well established and is based upon the observation of diabetics, who seem to age rapidly. The irreversible cross-linked proteins of AGEs in vessel collagen also contribute to atherosclerosis, as well as to kidney failure-conditions worsened in diabetes (*Diabetes* 46(supp2):S19-S25 (1997)). It is also believed AGEs aggravate protein cross-linking in plaques and tangles of Alzheimer's Disease, thereby accelerating neuron death (*Brain Research Review* 23:134-143 (1997)). When glucose bonds with collagen, many negative effects can result, including thickened arteries, stiff joints, feeble muscles and failing organs. As collagen molecules in the cartilage and skin have a long lifetime (117 years for cartilage and 15 years for skin collagen), they are susceptible to the accumulation of AGEs since the protein turnover is a major determinant in AGE accumulation (Verzijl N., et al., *J. Biol. Chem.* 275(50):39027-31 (2000)). Reducing glycation within the body to slow the aging process has been recommended to improve lifestyle and foster a youthful appearance. This has been done with food, guiding patients in what they eat, and how they cook. (F. Wilson, Cosmetic Surgery Times, September, 2004).

Currently, scientists believe there are two major ways in which AGEs can form inside the body. One way is through a simple series of chemical reactions known as the "Maillard Pathway," known from food chemistry for more than a century. During glycation, glucose binds to a protein bound nitrogen via a hydroxyl or carbonyl group. This intermediate then chemically rearranges to produce an Amadori product having two ketone groups on the second or third carbon of the glucose ring. This Amadori product goes through other rearrangements through the Maillard reaction. This is the basis for atherosclerosis, cataracts and other problems commonly associated with diabetes.

The second, discovered more recently, is based on a distinctly biological pathway, which only occurs within the cells because of the body's metabolism of carbohydrates or sugars. It is known that glucose and other saccharides are important glycating agents, but the most reactive glycating agents are the α-oxoaldehydes, glyoxal, methylglyoxal and 3-deoxyglucosone. Tissue-specific metabolic characteristics are understood to be involved in the degree of cellular protein modification by Maillard reactions, e.g., by modulation of the concentration of glycolysis intermediates or via specific defensive systems in these organs. (Portero-Otin, M., et al. *Biochem. Soc. Trans*. (2003) 31, 1403-1405.

AGEs are implicated as a major pathogenesis process in atherosclerosis, Alzheimer's Disease, the normal aging process, and the pathogenesis of the major microvascular complications of diabetes mellitus: nephropathy, neuropathy and retinopathy. In certain pathophysiological states, one or more of the following changes to glycation-related processes occurs: the rate of glycation is increased, the renal clearance of AGEs is decreased and/or the expression of AGEs receptors is increased leading to AGEs-related membrane thickening, AGEs-mediated cell activation, premature aging, and amyloidosis.

In the skin, glycation forms new AGEs in the extracellular matrix of the dermis and changes fibroblast shape and distribution, alters extracellular matrix molecules and the dermal-epidermal junction zone, increases β and α integrins concentration in the epidermal skin layer, and increases collagenase activity. (Pageon, H., et al., *Ann N Y Acad Sci.* 2005, 1043: 529-32.)

The mechanism of action for AGEs inhibitors is understood to include both nucleophilic traps for reactive carbonyl AGE intermediates and antioxidant activity. AGE inhibitors are chelators of copper, and potent inhibitors of ascorbate oxidation. Because of the strong ascorbate oxidization inhibition properties of AGE inhibitors, these properties are believed to be the primary mechanism for the inhibition of AGE formation. (Price D L, et al., *J Biol Chem.* 2001 Dec. 28; 276(52):48967-72). AGEs are primarily eliminated from the circulation by scavenger receptor-mediated uptake in hepatic sinusoidal endothelial cells. (Hansen, B. et al., *Diabetologia.* 2002 October; 45(10):1379-88).

There are several drugs that inhibit the formation of AGEs; one such candidate is aminoguanidine. Aminoguanidine is structurally very similar to guanidine, the active ingredient in the herb, goat's rue (*galega officinalis*). It is believed that aminoguanidine acts by enhancing the action of nitric oxide (Brownlee, *Diabetes,* 2:57-60 (1992)). However, recently aminoguanidine has shown signs of toxicity in human trials (Okada et al., *J. Nutr. Sci. Vitaminol.,* 41:43-50 (1995)).

In addition, it has been shown that thiamine pyrophosphate (TPP), the active coenzyme form of the B-complex vitamin thiamine, can stop late stage AGEs formation. TPP has also been shown to exert a two-pronged AGEs-inhibiting effect in the body. Boosting TPP in cells stressed by high glucose concentrations results in the opening of a "safety valve" in the normal metabolism of blood sugar through an enzyme known as transketolase. Activating transketolase allows the body to shunt excess triosephosphates, reactive glucose metabolic intermediates, transferring AGEs damage inside the cell into a safe alternative metabolic pathway, preventing their buildup and, concomitantly, preventing the formation of AGEs. Unfortunately, regular thiamine vitamin B is not readily absorbed and metabolized by the body. In addition, taking supplements comprising TPP is equally futile because specific enzymes strip TPP of its phosphate group, rendering the adulterated TPP ineffective to battle AGEs.

Another antiglycation compound, ALT-711, breaks the specific AGE-derived crosslinks between proteins, but does not disrupt the natural enzymatic glycosylation sites or peptide bonds of the collagen chain. ALT-711 has been shown to reduce age-related ventricular stiffness and improve cardiac function (Asif M, et al., *Proceedings of the National Academy of Sciences USA,* 97(6):2809-13; erratum:97(10):5679 (2000). ALT-711 also has been used to improve skin hydration of aged rats through oral and topical administration. (Vasan, S, et al., *Arch Biochem. Biophys.* 419(1):89-96 (2003).

Benfotiamine and B vitamins have previously been used in combination for the oral treatment of diabetic polyneuropathy (Stracke et al. *Clin. Endocrinol. Diabetes* 1996; 104(4): 311-6) and alcoholic polyneuropathy (Woelk H, et al., *Alcohol Alcohol.* 1998 November-December; 33(6):631-8). However, neither of these references suggest topical applications for treating aging skin.

While AGEs-inhibiting drugs have displayed promise in regard to treating a number of conditions, including the reduction in the signs of aging, there is a clear need for the identification of new, safe AGE-inhibiting, non-prescription topical compositions that can be used to address the signs of skin aging caused by reactive carbonyl species (RCS), glycation of skin proteins, formation of advanced glycation endproducts (AGEs) and formation of advanced lipoxidation endproducts (ALEs).

SUMMARY OF THE INVENTION

It is an object of the present invention to provide a method and composition for treatment and/or prevention of skin damage, particularly skin damage from RCS, glycation of skin proteins, and formation of AGEs and ALEs.

It is another and more specific object of the invention to provide a topical composition and method for an AGEs preventive regiment and/or therapy based upon topical application to exposed or affected skin areas of an active agent or derivative thereof, in association with a dermatologically acceptable carrier or vehicle.

These and other objects are accomplished by the present invention, which provides a method for inhibiting the formation of AGEs in the skin which comprises topical application to the exposed or affected skin areas of an effective amount of a combination of benfotiamine and pyridoxamine in a dermatologically acceptable carrier. Also provided is a method for the prevention and/or treatment of skin damage from AGEs, which comprises topical application to the exposed or affected skin areas of an effective amount of a combination of benfotiamine and pyridoxamine in a dermatologically acceptable carrier. The composition for the inhibition of the formation of AGEs and prevention and/or treatment of skin damage may be administered to a diabetic or a person without diabetes. Preferably, the composition is administered to anyone with skin damage from AGEs, including damage caused by chronological aging and damage caused by photoaging.

In the preferred practice of the invention, the combination of benfotiamine and pyridoxamine is applied in admixture with a dermatologically acceptable carrier or vehicle (e.g., as a lotion, cream, ointment, soap, or the like) so as to facilitate topical application and, in some cases, provide additional therapeutic effects as might be brought about, e.g., by moisturizing of the affected skin areas. Additionally, other ingredients, particularly antioxidants, can be advantageously included in the compositions.

The amount of benfotiamine and the amount of pyridoxamine necessary to bring about enhanced prevention and/or therapeutic treatment of skin damage is not fixed per se, and is necessarily dependent upon the identity and form of pyridoxamine and benfotiamine employed, the amount and type of any additional ingredients used, particularly those that appear to exhibit synergistic effects (to be discussed more fully below), the user's skin type and, where present, the severity and extent of the patient's pathological skin condition. Generally, the benfotiamine and/or pyridoxamine or composition containing it is topically applied in effective amounts to skin areas which have been damaged or aged, or which are susceptible to damage because of AGEs.

In one embodiment, the composition contains from about 0.001 to 80 weight %, preferably from about 0.1% to about 5%, of each of benfotiamine and pyridoxamine.

DETAILED DESCRIPTION OF THE INVENTION

This invention is based upon the finding that a combination of the two AGE inhibitors benfotiamine and pyridoxamine is useful for the treatment and prevention of damaged or aged skin from reactive carbonyl species (RCS), glycation of skin proteins, formation of advanced glycation endproducts (AGEs) and formation of advanced lipoxidation endproducts (ALEs).

I. Benfotiamine

As used herein the term "a benfotiamine" encompasses benfotiamine ([4-[(4-amino-2-methyl-pyrimidin-5-yl)methyl-formyl-amino]-3-benzoylsulfanyl-pent-3-enoxy]phosphonic acid), which has the formula:

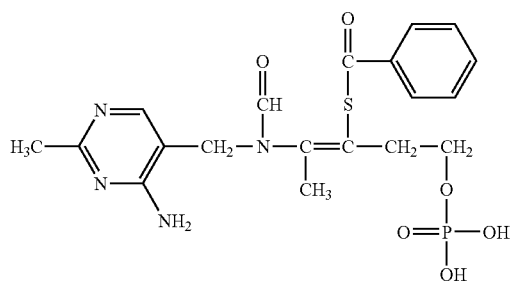

The term a benfotiamine also encompasses benfotiamine derivatives such as S-Benzoylthiamine O-monophosphate and benzoylthiamine, which has the following formula:

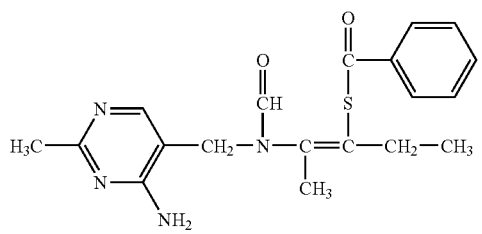 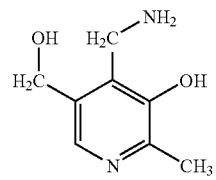

Benfotiamine is the most potent of the allithiamines, a unique class of thiamine-derived compounds present in trace quantities in roasted crushed garlic and other vegetables from the *Allium* genus (such as onions, shallots and leeks).

Benfotiamine raises the blood level of thiamine pyrophosphate (TPP, or thiamine diphosphate), which is the biologically active co-enzyme of thiamine. TPP plays an essential role in the Kreb cycle by removing $CO_2$ from pyruvic acid, making TPP vital to the production of cellular energy. (See Stryer, Biochemistry, $3^{rd}$ ed. W.H. Freeman and Co. New York 1988). Benfotiamine's unique open-ringed structure facilitates its passage directly through cell membranes, readily crossing the intestinal wall and being taken straight into the cell. As a result, the body readily absorbs benfotiamine better than thiamine itself, and plasma levels of thiamine and thiamine pyrophosphate (TPP) remain higher for longer. Thiamine absorption from benfotiamine is about five times as great as from conventional thiamine supplements, and benfotiamine is less toxic than conventional thiamine supplements. By effectively increasing levels of TPP, benfotiamine decreases the formation of AGEs. In one embodiment, thiamine is added to the topical formulation in addition to the benfotiamine to enhance the effect.

Benfotiamine has also been shown to be useful in treating patients with diabetic neuropathy due to the anti-glycation effects of the agent (Haupt, E., et al., *Int J Clin Pharmacol Ther.* 2005 43(2):71-7.) Both thiamine and benfotiamine have been shown to prevent the development of incipient nephropathy by halting the increase in hydroimidazolone AGE residue formation (Karachalias, N, et al., Ann N Y Acad Sci. 2005 June; 1043:777-83). Additionally, benfotiamine has been found to help maintain healthy cells in the presence of blood glucose by stimulating tranketolase, a cellular enzyme essential for maintaining normal glucose metabolic pathways (Obrenovich M E et al, *Sci. Aging Knowledge Environ.* 2003 Mar. 12; 2003(10):PE6; Hammes, H P, Nat Med. 2003 March; 9(3):294-9). Benfotiamine directs hexose and triose phosphates to the pentose phosphate pathway, and reduces tissue AGEs. Similar improvements in nerve and vascular function have been observed (Cameron, N E et al., *Ann N Y Acad Sci.* 2005 June; 1043:784-92). This enhancement of energy metabolism is also important for the aging process as cellular energy declines with aging. (Squier, T C, *Exp Gerontol.* 2001 September; 36(9):1539-50). Therefore the use of a formulation comprising benfotiamine particularly useful as it has a multipronged effect in targeting the aging process especially when combined with an additional cellular energy enhancing agent.

II. Pyridoxamine

As used herein the term "a pyridoxamine" encompasses 4-aminomethyl-5-hydroxy-6-methyl-3-pyridinemethanol (pyridoxamine), which has the following structure The term a pyridoxamine also encompasses pyridoxamine derivatives such as 4-amino-methyl-5-hydroxy-6-methyl-3-pyridinemethanol dihydrochloride, and 4-aminomethyl-5-hydroxy-6-methyl-3-pyridylmethyl phosphate.

Pyridoxamine is a vitamin B6 derivative that is water-soluble and nontoxic in rats and humans. It inhibits the formation of AGEs from Amadori proteins and is classified as a post-Amadori inhibitor (Khalifah et al. *Biochem. Biophys. Res. Comm.* 199:257, p. 251-258). Other AGE inhibitors such as aminoguanidine are primarily scavengers which scavenge reactive dicarbonyl precursors to AGEs (Khalifah R G, et al., *Ann N Y Acad Sci.* 2005 June; 1043:793-806). Pyridoxamine sequesters catalytic metal ions and blocks oxidative degradation of Amadori intermediate. It also actively scavenges the toxic carbonyl products of sugar and lipid degradation and inhibits reactive oxygen species (Voziyan, P A., *Ann N Y Acad Sci.* 2005; 1043:807-16; Voziyan, P A et al., *Cell Mol Life Sci.* 2005; 62(15):1671-81.) It is also believed that pyridoxamine traps reactive dicarbonyl intermediates in AGE formation and may also decrease oxidative stress, which subsequently decreases AGE formation from reactive oxygen species (Iacovella et al. *SCJMM,* 2004: 5, p. 73-101).

Pyridoxamine has also been shown to inhibit advanced lipoxidation end products (ALES) (Onorato J M. et al., *J. Biol. Chem.* 275(28):21177-84 (2000)). Malondialdehyde, (an intermediate in the formation of ALEs during lipid peroxidation) is trapped under physiological conditions by pyridoxamine and inhibits the formation of ALEs (Kang, Z et al., *Amino Acids.* 2005 Jul. 5 (epub)). Decreasing ALEs formation is accomplished by decreasing the concentration of an oxidiable substrate such as glucose and blood lipids (Metz T O, et al., *Arch Biochem Biophys.* 419(1):41-9 (2003)). It has been proposed that the antioxidant properties of pyridoxamine be used for the inhibition of ALE as well as AGE formation and development of complications of diabetes and hyperlipidemia (Mene P, et al., *Am J Cardiovasc Drugs.* 3(5):315-20 (2003)). The ALEs inhibiting property of ayridoxamine is significant as peroxidation of skin lipids is a factor in skin damage and aging.

Pyridoxamine, as well as the other B vitamins pyridoxine and pyridoxal, is metabolized in the liver to pyridoxal-5'-phosphate, the active form of the vitamin. For a general review of the vitamin B complex see *The Pharmacological Basis of Therapeutics,* 8th edition, ed. Gilman, Rall, Nies, and Taylor (Pergamon Press, New York, 1990, pp. 1293-4; pp. 1523-1540). Although it has long been believed that these three forms have equivalent biological properties, this has been shown to be incorrect. They have different antioxidant activities (i.e., the efficacy order is pyridoxal 5'-phosphate≧pyridoxamine 5'-phosphate>pyridoxamine>pyridoxal≧pyridoxine. Pyridoxamine and the two phosphates have greater antioxidant activity than Vitamin C (Chumnantana, R., *Biochim Biophys Acta.* 2005, 11; 1722(1):84-91. Epub 2004 Dec. 19). U.S. Pat. Nos. 6,750,209 and 6,740,668 demonstrate the difference in pyridoxamine and the other B6 vitamins as inhibitors of post- Amadori antigenic AGE formation. The efficacy of inhibition of overall glycation of protein, in the presence of high concentrations of sugar, was not predictive of the ability to inhibit the post-Amadori steps of AGE formation where free sugar is removed. Pyridoxamine has strong antioxidant activity and has been shown to be the strongest AGE inhibitor of the B vitamins, and is therefore preferred in the topical formulations of the present invention (Price, D. L., J. Biol. Chem. 2001 Dec. 28; 276(52):48967-72.)

Pyridoxamine is also particularly beneficial due to its low toxicity compared to pyridoxine. Pyridoxamine does not cause injury to the primary sensory neurons as does pyridoxine (Levine, S., J Appl Toxicol. 2004 November-December; 24(6):497-500.) Due to the safety, its strength as an AGE inhibitor, and its strength as an antioxidant, pyridoxamine is significantly more useful than pyridoxine (a compound used extensively as a vitamin B6 agent in topical formulations).

III. Combinations

In accordance with this invention, by combining a benfotiamine and a pyridoxamine, there is a decrease in their toxicity profiles or the potential of a skin irritation in sensitive individuals. An enhanced efficacy of AGE inhibiting capabilities when a benfotiamine and a pyridoxamine are administered in combination also occurs. A topical composition comprising both a benfotiamine and a pyridoxamine is markedly superior to a composition having only a single AGE-inhibiting compound. Since the two AGE inhibitors work in different ways by inhibiting the pathway to AGEs at different stages; there is an enhanced effect when pyridoxamine and benfotiamine are combined compared to the use of a single one of the AGE inhibitors. Therefore, there is a beneficial for use on skin, such as on the face, neck, and hands, to relieve the effects of damage from reactive carbonyl species (RCS), glycation of skin proteins and formation of advanced glycation endproducts (AGEs).

Benfotiamine and pyridoxamine are both inhibitors of AGE. Additionally, they all have other benefits that, when combined into a formulation, provide AGE inhibition using lower concentrations of the components than would be required if a single agent were used. The reduced concentrations of benfotiamine and pyridoxamine decrease the toxicity effects of these agents and their potential of irritating skin in sensitive individuals.

Additionally, benfotiamine, pyridoxamine, and other agents described herein incorporated in the formulation of the present invention provide other benefits as well. For example, benfotiamine, as a precursor for TPP, increases the amount of TPP in the blood and decreases pyruvic acid concentration in a process that converts pyruvic acid into COA. Pyridoxamine lowers the toxicity of agents such as carnosine, a preferred additional AGEs inhibitor in this invention; decreases oxidative stress; and inhibits ALE formation. Carnosine, one preferred additional agent, is also a potent anti-glycation agent, promotes wound healing, and protects against radiation damage. Additionally, where the formulation induces lower pyruvic acid levels due to the presence of a benfotiamine, carnosine is better able to reduce glycolysis intermediates compared to other formulations. (Holliday, R. *Br J Cancer.* 1996 April; 73(8):966-71). Therefore a formulation containing pyridoxamine, benfotiamine and carnosine is superior to a formulation containing benfotiamine or pyridoxamine alone. Additionally, a formulation combining benfotiamine and pyridoxamine is beneficial compared to a formulation with only one of these components because of the added benefits of the two components. For example, benfotiamine increases TPP and therefore contributes to DNA and RNA formation via the transketolase pathway as well as increasing cellular energy via Coenzyme A, and pyridoxamine decreases oxidative stress and inhibits ALEs formation. Adding additional components such as carnosine adds even more unique functions to the formulation of the present invention because, for example, carnosine is also a potent anti-glycation agent and has other beneficial properties discussed in this application.

As used herein, the term "treatment of skin damage" means the treatment of the symptoms of skin damage, treatment of the skin to prevent or reduce the damage from reactive carbonyl species (RCS), glycation of skin proteins, formation of advanced glycation endproducts (AGEs) and formation of advanced lipoxidation endproducts (ALEs) and/or to prevent or reduce the further accumulation of reactive carbonyl species (RCS), glycated skin proteins, advanced glycation endproducts (AGEs) and advanced lipoxidation endproducts (ALEs) in the skin.

The skin damage from AGEs as well as ALES in the skin include elastosis; atrophy; wrinkling; vascular changes including diffuse erythema, ecchymoses, and telangiectasias; and pigmentary changes including lentigines, freckles, and areas of hypo- and hyper-pigmentation. This damage is reduced, and further damage can be reduced or prevented by the topical administration of benfotiamine and pyridoxamine. This damage can be described by the effects of glycation in the skin, which has been shown to (1) modify fibroblast shape and distribution; (2) enhance extracellular matrix molecules and the dermal-epidermal junction zone; (3) increase $\beta_1$ and $\alpha_6$ integrin concentration in the epidermal cell layer; and (4) increase collagenase activity. When an AGE inhibitor is topically applied to the skin, these markers overexpressed in glycated skin constructs are reduced and the visible effects of. (Pageon, H., et al., *Ann N Y Acad Sci.* 2005, 1043:529-32.)

Only effective amounts of a benfotiamine and a pyridoxamine are needed to prevent or treat skin damage caused by AGEs. Generally, an effective amount of the topical formulation is applied to exposed or affected skin sites in association with a carrier, and particularly one in which the active ingredient is soluble per se or is effectively solubilized (e.g., as an emulsion or microemulsion). It is necessary that the carrier be inert in the sense of not bringing about a deactivation of a benfotiamine and/or a pyridoxamine, and in the sense of not causing any adverse effect on the skin areas to which it is applied.

By the term "an effective amount" or "amount effective" of a compound or property, e.g., an amount effective in reducing or eliminating the effects of AGE as provided herein, is meant such amount as is capable of performing the function of the compound or property for which an effective amount is expressed. As pointed out above, the exact amount required will vary from case to case, depending on recognized variables such as the compounds employed and the individual subject treated. Thus, it is not possible to specify an exact "effective amount." However, an appropriate effective amount may be determined by one of ordinary skill in the art using only routine experimentation.

In one embodiment, one or more of the active components of the formulation, and preferably all of the active components (including additional agents) are from a natural source or are nature-identical. The term "nature-identical" includes synthetic compounds having the same chemical structure, regioisomeric form and stereoisomeric form as compounds produced by either a plant or animal. Natural and nature-identical compounds are preferred in a particular embodiment of the present invention since different isomers and synthetic chemicals with novel molecular structures can have unpredictable effects on skins metabolism and many are unlikely to be biodegradable.

The combination of benfotiamine and pyridoxamine is particularly useful in a topical formulation when the skin and/or underlying tissue or the topical and/or oral formulation contains a high concentration of a saccharides, Vitamin C, amino acids prone to glycation, and the like. In the personal care industry, there are many substances that can lead to AGEs that are increasingly being used for their skin benefits as functional ingredients (e.g., sugars as humectants, sugar derived emulsifiers or surfactants) or actives (ascorbate, pufas, amino acids). The topical benfotiamine and pyridoxamine formulation eliminates or decreases the potential antiglycation effects of these substances, allowing these nutrients to open their full beneficial potential. One example of this is the use of ascorbic acid (i.e., vitamin C) in topical formulations. This easily oxidizable compound is increasingly being used in topical products. Its oxidized form is dehydroascorbate, a species which leads to the formation of AGEs. Therefore, the present invention is particularly useful in combination with topical formulations containing vitamin C. Similarly, these compounds may have been ingested orally to create the high concentration of the agents in the skin and/or underlying tissue. For example, sugars are added to a number of food products. In particular, fructose is added to products to provide a 'natural' sugar which many consumers feel is beneficial. However, fructose glycates four or five times faster than glucose. (Wilson, F. *Cosmetic Surgery Times*, September, 2004). Therefore, the topical formulation of the present invention is particularly useful when the skin, underlying tissue, a topical administration (either in the same formulation or in a separate formulation), an oral administration, or a combination thereof contains a high concentration of agents prone to glycation or agents whose oxidation product are prone to glycation or agents included for other beneficial properties that are themselves glycating agents.

IV. Additional Ingredients

Many preferred embodiments of this invention contain at least one or more other active ingredients in addition to benfotiamine and pyridoxamine. Such additional active ingredients may include, but are not limited to, compounds known to inhibit the formation of AGEs, antioxidants, sunscreens glutathione, SOD, r-lipoic acid and its derivatives catalase, an energizing ingredient (e.g., mitochondrial resuscitants), acetylcholine and choline containing natural ingredients, acetylcholine or choline precursors or metabolites, cholinesterase inhibitors and acetyl-cholinesterase inhibitors, matrix metalloprotease inhibitors, dermorelaxants, anti-inflammatory agents, molecular film tensors, alpha hydroxy acids, salicylic acid, ascorbic acid and its derivates and collagen protecting or collagen increasing agents.

AGE inhibitors

An additional agent that may be added to the pyridoxamine and benfotiamine formulation of the present invention is an anti-glycation agent. As used herein, the term "anti-glycation agent" means a compound for preventing and/or reducing the glycation of skin proteins, in particular of dermal proteins such as collagen. The anti-glycation agent inhibits the formation of advanced glycation end products (AGEs) and is also known as an AGE inhibitor.

Strong antiglycation compounds are preferentially added to the benfotiamine and pyridoxamine formulation as they increase the AGE inhibitory potential of the formulation, can have a different, and often complementary, inhibitory mechanism, and may have very strong antiglycation properties regarding collagen specifically.

A non-limiting list of examples of anti-glycation agents are aminoguanidine, ALT-946, OPB-9195, alagebrium chloride, N-phenacylthiazolium bromide, LR-90, plant extracts of the Ericaceae family, such as an extract of blueberry (*Vaccinium angustifolium*); ergothioneine and its derivatives; and hydroxystilbenes and their derivatives, such as resveratrol and 3,3',5,5'-tetra-hydroxystilbene. Other exemplary inhibitors of AGE formation include, but are not limited to, thiamine, G-rutin (Nagasawa T., *Mol Cell Biochem.* 249(1-2):3-10, 2003); pyridoxal phosphate, aminoguanidine, a aminoguanidine-pyridoxal adduct, green tea (Ouyang P. *Di Yi Jun Yi Da Xue Xue Bao* 24(3): 247-51, 2004); extracts of *Thymus vulgaris* (Morimitsu et al., *Biosci Biotechnol Biochem* 59(11):2018-21, 1995); Ge-132(2-carboxyethyl germanium sequioxide) (Unakar et al., *Exp. Eye Res.* 61(2): 155-64, 1995); curcumine (Sajithlal et al., *Biochem Pharmacol.* 56(12):1607-14, 1998); extracts of *Cratoxylum cochinchinense* (Tang, S Y et al., *Free Radic. Biol. Med* 36(12):1575-87, 2004); extracts of *Apocynum venetum Luobuma* (Yokozawa et al., *Food Chem. Toxicol.* 42(6):975-81, 2004); carnosine; carnosinylated proteins (Hipkiss A R et al., *Cell Mol Life Sci.* 57(5):747-53, 2000); extracts of *Eugenia bicyclis* (Okada et al., *Nat. Prod.* 67(1):103-5, 2004); rutin (Kiho, T et al., *Biosci. Biotechnol. Biochem.* 68(1):200-5, 2004); amadoriase enzymes from *Aspergillus fungi* (Monnier V M et al., *Biochem. Soc. Trans* 31:1349-53, 2003; U.S. Pat. No. 6,605,642), guanidine rich extracts of *Galega officinalis*, and extracts of *lycopersicon esculentum*. The AGE inhibitor as described herein may be incorporated in amounts from about 0.001%-30% by weight. More preferably, the AGE inhibitor is incorporated in amounts from about 0.1%-5% by weight, based on the total weight of the preparation. For compounds without a recommended daily dose, the dose will be within the range commonly accepted as safe and effective for that particular compound.

A preferred anti-glycation agent is carnosine. As used herein the term "carnosine" encompasses the dipeptide beta-alanyl-L-histidine; it includes D,L-carnosine, D-carnosine, L-carnosine and their derivatives (for example, anserine), as well as their salts (for example, zinc carnosine, copper carnosine, and copper anserine).

Carnosine has been shown to possess strong and specific antioxidant properties. It is a potent anti-glycation agent and has unique anti-aging properties. It has a free-radical scavenging activity and has been shown to extend human fibroblast life-span, kill transformed cells, protect cells against aldehydes and amyloid peptide fragments and inhibit, in vitro, DNA/protein cross-linking, and act as an aldehyde scavenger (Hipkiss, A R, *Int J Biochem Cell Biol.* 1998 August; 30(8):863-8; Hobart et al. *Life Sci.* 75:1379-89.) It also promotes wound healing (Roberts P R, et al., *Nutrition* 1998; 14; 266-9), protects against radiation damage, is potentially a modulator of enzymatic activities, and has been shown to be a chelator of heavy metals (Quinn, P J et al., Mol. Aspcts Med. 1992; 13(5), 379-444; (Hipkiss A R. *Int J Biochem Cell Biol* 1998; 30:863-8). Carnosine is degraded by histidine and carnosinase to form histamine and β-alanine (Nagai, K et al., Surgery 1986, 100(5); 815-821.) The β-alanine produced by the degradation of carnosine stimulates the biosynthesis of nucleic acids and of collagen. This increased collagen synthesis is an important aspect of the present invention, as it provides additional benefit to the skin and reduces the effects of aging. Similarly, the histamine produced by the degradation process stimulates early effusion at the initial stage of tissue inflammation. Researchers have hypothesized that the effectiveness of carnosine stems from its ability to react with carbonyl groups on glycated or oxidized proteins (i.e., carnosinylation); this reaction inhibits the glycoxidised proteins from cross-linking with normal macromolecules and causing the signs of aging (Hipkiss A R, et al., Mech Ageing Dev 2001 Sep. 15; 122(13):1431-45; Hobart et al. Life Sci. 75:1379-89).

Carnosine reacts strongly with aldehyde and keto groups of sugars by Amadori reaction, and is also theorized to deplete certain glycolysis intermediates. Therefore, a reduction of glycolysis intermediates by carnosine depletes their energy supply. But the addition of pyruvate reverses this effect (Holliday R Br J Cancer. 1996 April; 73(8):966-71). Therefore, it is preferable to add carnosine to a formulation which also reduces the amount of pyruvate available. Additionally, the reaction between carnosine and aldehydes protects susceptible macromolecules. Therefore, carnosine inhibits nonenzymic glycosylation and cross-linking of proteins induced by reactive aldehydes (aldose and ketose sugars, certain triose glycolytic intermediates and malondialdehyde (MDA), a lipid peroxidation product) (Hipkiss A R, et al., Ann NY Acad Sci. 1998 Nov. 20; 854:37-53). Carnosine has also been shown to be beneficial on growth, morphology, and longevity of cultured human fibroblasts, and has an important role in cellular homeostasis and maintenance (McFarland G A, et al, Exp Gerontol. 1999 January; 34(1):35-45).

Amyloid beta peptides enhance the expression of AGE receptors (Chaney, M O, et al., Biochim Biophys Acta. 2005 Jun. 30; 1741(1-2):199-205. Epub 2005 Apr. 19). These receptors mediate amyloid-beta peptide transport across the blood-brain barrier, suppress cerebral blood flow, exaggerate cell stress, and increase the signs of aging in the skin. Production of the AGE-crosslinked amyloid peptide aggregates has been shown to be attenuated by carnosine (Munch, G., et al., Biochim Biophys Acta. 1997 Feb. 27; 1360(1):17-29). These protective effects are attributed to its anti-glycating and antioxidant activities (Preston, J E, et al., Neurosci Lett. 1998 Feb. 13; 242(2):105-8).

One general problem with the administration of carnosine is that the β-alanine metabolite can have some toxic effects on cell growth. Beta-alanine has been shown to reduce skin fibroblast cell growth; however, the co-administration of pyridoxamine can be used to significantly reduce these β-alanine toxic effects (Higgins J. J., et al., Neurology. 1994 September; 44(9):1728-32). When carnosine is chelated to zinc or copper ions, the presence of the ions enhances carnosine's activity as a superoxide radical scavenger (Gulyaeva N Y, Biochemistry 57 (7:2) 1051-4, 1987). Therefore, the addition of carnosine as an agent in the present invention provides for superoxide scavenger activity as well as the anti-glycation and anti-oxidation properties of carnosine. Carnosine has been administered orally at dosages above 500 mg/kg body weight in animal studies and has found to be safe. The addition of carnosine in the formulation of the present invention will be between 0.001-10% by weight.

The salts and derivatives of carnosine are also useful additions to the present invention and salts and derivatives thereof, which function as a pH buffer and also act as an agent of inhibiting protein cross-linking. One preferred embodiment uses N-acetyl-carnosine as it is highly resistant to hydrolysis by carnosinases and therefore may provide protection from AGEs for a longer period of time in comparison to carnosine. Zinc and copper complexes of carnosine are also useful as chelating agents (Kohen et al., Free Radic. Res. Commun. 991; 12-13 Pt 1:179-85).

A topical composition comprising a carnosine, a lipoic acid such as R-lipoic acid or R-dihyrolipoic acid, and a carnitine such as acetyl-1-carnitine, may be combined with the formulation of the present invention. This formulation, which is useful in improving the appearance of aged skin characterized by wrinkles and loss of elasticity, and has been described in U.S. Prov. Pat. Appl. 60/665,206 filed Mar. 24, 2005, herein incorporated by reference.

An anti-glycation agent of interest is garcinol. Garcinol occurs naturally in the latex exudate of the herb Garcinia Cambogia, which is used as a weight loss supplement. Garcinol is a moderate antioxidant, metal chelator, and free radical scavenger. It also is a superoxide anion scavenger and has been shown to suppress glycation in a bovine serum albumin/fructose system. (Yamaguchi F. et al., J Agric Food Chem. 2000 February; 48(2):180-5) It has also been shown that the (−)-hydroxycitrate from Garcinia fruits may aid endurance during post-absorptive aerobic exercise by promoting gluconeogenesis. Garcinia is particularly useful as an additional agent because the combination of garcinol with carnitine and chromium will have anti-glycation properties and promote gluconeogenesis (McCarty M F. Med Hypotheses. 1995 September; 45(3):247-54).

Aglycal LS 8777, made by Laboratoires Serobiologique (Cognis France), may also be included as an anti-glycation agent in the formulation of the present invention. Aglycal LS 8777 is a plant-based complex that retards the glycation of proteins. This photo-complex aids in the long-term elasticity of the skin and protects against the fragmentation of collagen. (www.laboratoires-serobiologiques.com)

Aldenine, made by Lipotec (Spain), is a complex of a tripeptide and hydrolyzed wheat and soy proteins that boosts Collagen III synthesis while protecting cells from photo damage. Aldenine detoxifies the skin from harmful RCS (Reactive Carbonyl Species).

Another anti-glycation agent, ANTIGLYSKIN® from Silab, is rich in phenolic acids and glycopeptides from sunflower and inhibits the protein glycation reaction and prevents the glyco-oxidation.

Compounds obtained from Pterocarpus marsupium may also be incorporated into the topical formulation. (−) Epicatechin, the active ingredient in the Indian herb Pterocarpus marsupium Roxb, can be obtained from the water extract of the bark and is insulinogenic. (Ahmad F, et al., Acta Diabetol Lat. 1989 October-December; 26(4):291-300). It has been found to decrease hepatic and skeletal muscle glycogen (Grover J K, et al., Mol Cell Biochem. 2002 December; 241 (1-2):53-9). In addition, three flavonoid antioxidants are also present in the heartwood; these flavonoid are marsupsin, pterosupin, and liquiritigenin. The gum tannic acid and a non-glucosidal tannin, kino tannic acid, and Pterocarpus marsupium extracts have also been shown to have anti-oxidant activity (Katiyar S K, et al., Photochem Photobiol. 1995 November; 62(5):855-61) and a strong anti-glycation agent (www.laboratoires-serobiologiques.com/LSvi/english/prod_2.html)).

N-Acetylcysteine is an N-acetylated cysteine which is a thiol containing amino acid, also called α-acetamido-β-mercaptopropanoic acid, which is a preferred additional component of the present invention. The incorporation of N-acetylcysteine into the topical formulation will improve the signs of aging of the skin. N-acetylcysteine is an antioxidant and also has been indicated as protective against pulmonary oxygen toxicity (Eur. Respir. J. 2: 116-126 (1989)). It is also an anti-glycation agent. Preferred forms of N-acetyl cysteine include: N-acetyl-L-cysteine, N-acetyl-L-cysteine amide, N-acetyl-L-cysteine methyl ester, N-acetyl-L-cysteine ethyl ester, N-acetyl-L-cysteine propyl ester, and N-acetyl-L-cysteine isopropyl ester. See PCT US96/16534 which teaches topical compositions containing N-acetylcysteine, and U.S.

application Ser. No. 20030229141 which discloses the topical use of N-acetyl cysteine to alleviate or improve various cosmetic conditions and dermatological disorders.

AGE inhibitors that may be added to the formulation include the enzymes, fructosyl lysine oxidase and fructose lysine 3-phosphokinase, which catalyze the deglycation reaction and generate free amine groups. The biochemical properties of these amadoriase enzymes and their role in protein deglycation are described by Wu, X et al., Arch Biochem Biophys. 419(1):16-24 (2003). See also Takahasi, M. et al., J. Biol. Chem. 272, 3437-43 (1997). The amadoriase enzymes are particularly useful since they have strong anti-glycation activity, and some of these compounds are selective for collagen. This makes these enzymes particularly useful as components in the topical formulation of the present invention since they will preferentially act on collagen and therefore inhibit the glycation of collagen and reduce the signs of aging in the skin.

Another class of AGE inhibitors that may be used in the formulation of the present invention is described by Rahbar et al., Molecular Cell Biology Research Commun. 3, 360-66 (2000). These compounds are benzoic acid derivatives, aryl and heterocyclic ureido compounds, and aryl and heterocyclic carboxamido phenoxy isobutyric acids. They have been shown to be potent inhibitors of glycation, and have been shown to inhibit the glycation of collagen.

Other AGE inhibitors are described by M Takahashi et al., who teache the isolation, purification, and characterization of amadoriase isoenzymes (fructosyl amine-oxygen oxoreductase) (J. Biol Chem. (1997) J. Biol Chem. 272, 3437-3743).

Additionally, antiglycation compounds may be added to the pyridoxamine and benfotiamine formulation. Two types of enzymes, fructosyl lysine oxidase and fructose lysine 3-phosphokinase, catalyze the deglycation reaction and generate free amine groups. The biochemical properties of these amadoriase enzymes and their role in protein deglycation are described by Wu, X et al., Arch Biochem Biophys. 419(1):16-24 (2003). In one embodiment, the compounds described by Wu, Takahasi, and/or Rahbar are used in combination with the formulation described herein. The compounds described by Wu, Takahasi, or Rahbar may be used in combination with the formulation described herein.

Other AGE inhibitors may be added to the formulation of the present invention. Extracts of *Paeonia suffruticosa* have been shown to be AGE inhibitors (Okano et al., at www.creative-developments.co.uk/papers/Natural%20Ingredients%201998.html). Additionally, AGE inhibitors have been isolated along with compounds having antioxidant activity from *Paeonia suffruticosa*; these compounds include the monoterpene glycoside, α-benzoyloxypaeoniflorin, β-benzoyloxypaeoniflorin, paeonolide, paeoniflorin and mudanpioside H. (Ryu G., et al, Arch Pharm Res. 2001 April; 24(2):105-8).

Another AGE inhibitor is from extracts of *Sanguisorba officinalis*, which has been shown to reduce chronic photodamage to the skin. (Tsukahara K., Biol Pharm Bull. 2001 September; 24(9):998-1003). *Pterocarpus marsupium* has been shown to be an anti-diabetic agent and strong antihyperglycemic agent (Babu P S., J. Pharm Pharmacol. 2004 November; 56(11):1435-42). *C. Cochinchinense* has been found to be a particularly potent AGE inhibitor on proteins and also to strongly inhibit hypochlorous acid-induced DNA damage. (Tang S Y, Free Radic Biol Med. 2004 Jun. 15; 36(12):1575-87).

There are other natural products that are AGE inhibitors, which may be used in the present invention. The screening method described by Matsuura, based on a fluorometric analysis, may be used to determine the inhibitory index of the Maillard reaction and AGE inhibition to determine compounds useful to include in the formulation of the present invention. (Nobuyasu Matsuura et al. J. Health Science 48(6) 520-526 (2002)). In addition new AGE inhibiting compounds may be synthesized by molecular combination of two or more AGE inhibitors. These newly created molecules would need to be tested for their AGE inhibiting properties as well as their safety and efficacy before they can be incorporated into the formulation. RCS (reactive carbonyl species) are detoxified by several enzymatic pathways, such as aldose reductase, aldehyde dehydrogenases, and the glyoxalase pathway. These enzymes produced via biotechnology can be also incorporated in the formulation.

Antioxidants

In particular, preferred embodiments of the additional active ingredients included in the formulations of the present invention are compounds having antioxidative action due to their known benefit in protecting the skin and the implication of oxidative stress in the formation of RCS as well as to protect from the known oxidative stress created by AGEs. Exemplary antioxidants include, but are not limited to, amino acids (e.g. glycine, histidine, tyrosine, and tryptophan) and their derivatives, imidazoles (e.g. urocanic acid) and their derivatives, carotenoids (e.g. lutein, lycopene), carotenes (e.g. α-carotene, β-carotene, lycopene, canthaxantin, cryptoxanthin, zeaxanthin and astaxanthin) and their derivatives, chlorogenic acid and its derivatives, aurothioglucose, propylthiouracil, thiotaurine and other thiols (e.g. thioredoxin, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, aminoethylcysteine, decarboxylated dimmer of aminoethylcysteine ketimine, dilauryl thiodipropionate, distearyl thiodipropionate, thiodipropionic acid and their derivatives (esters, ethers, peptides, lipids, nucleotides, nucleosides and salts) and sulphoximine compounds (e.g. buthionine sulphoximines, homocysteine sulphoximine, buthionine sulphones, pentathionine sulphoximine, hexathionine sulphoximine, heptathionine sulphoximine) in very low, acceptable doses; also (metal) chelating agents (e.g. α-hydroxy fatty acids, palmitic acid, phytic acid, lactoferrin, tannins, and curcumine), α-hydroxy acids (e.g. citric acid, lactic acid, malic acid, mandelic acid), humic acid, colic acid, colic extracts, bilirubin, biliverdin, EDTA, EGTA and their derivatives, unsaturated fatty acids and their derivatives (e.g. γ-linolenic acid, linolic acid, oleic acid), folic acid and their derivatives, ubiquinone and ubiquinol and their derivatives, vitamin A and derivatives (e.g. vitamin A palmitate), the other B vitamins and their derivatives, including thiamine, coniferyl benzoate of benzoin resin, rutinic acid and their derivatives, butylhydroxy toluene, butylhydroxy anisole, nordihydroguaiacic acid, nordihydroguaiaretic acid, trihydroxybutyrophenone, uric acid and its derivatives, mannose and its derivatives, sesamol, sesamolin, zinc and its derivatives (e.g. ZnO, $ZnSO_4$) including zinc amino acid chelates (zinc-methionine, zinc acetyl-methionate), selenium and its derivatives (e.g. selenium methionine), stilbenes and their derivatives (e.g. stilbene oxide, trans-stilbene oxide), proanthocyanidins, ascorbic acid, particularly fat-soluble fatty acid esters of ascorbic acid (e.g. ascorbyl palmitate and tetrahexydecyl ascorbate), quercetin and its derivatives (e.g. quercetin glycoside or rutin), hesperidine, sylimarin, sylibin, glabridin, superoxide dismutase and their derivatives, catalase and its derivatives, carnosic acid and its derivatives, apigenin and its derivatives, luteolin and its derivatives, chlorogenic acid and its derivatives, caffeic acid and its derivatives, ferrulic acid and its derivatives, resveratrol and its derivatives, green tea polyphenols and its derivatives, matrix metalloproteinase inhibitors (e.g. green tea polyphenols, trans-retinoic acid, luteoline, quercetine, ursolic acid, shark cartilage preparations, diterpenes and ursolic acid from Siegesbeckia and Centaurium extracts, and α tocopherol), Coenzyme Q10, glutathione and its derivatives, myristicin, changkil saponins (from *platycodon grandiflorium*, which is also known as jie geng), pomegranate, ellagic acid, honokiol (from *magnolia officinalis*), magnolol (from *magnolia officinalis*), naringenin, clove essential oil, martynosides, verbascosides, wolfberry (from *lycium barbarum*) extracts, cascading antioxidants including but not limited to carnosic acid, standardized extract of *Phyllanthus emblica* (trade named Emblica), pinus maritima and pinus radiata bark extracts, hydroxytyrosol (from olives), genistein, thiotaurine, antioxidants from marine species (e.g., Bioplasma® and monostrama extract from Secma), roxisomes (from AGI), crocetin, pine pollen extracts, beta glucans and the suitable derivatives of the invention (salts, esters, ethers, sugars, nucleotides, nucleosides, peptides and lipids) of these said active ingredients.

Anthocyanins and their derivatives are particularly preferred antioxidants. Anthocyanins encompasses a class of flavonoid compounds that are naturally occurring, water-soluble compounds, responsible for the red, purple, and blue colors of many fruits, vegetables, cereal grains, and flowers. Anthocyanins are susceptible to degradation by light, heat, oxygen, and other reactants including iron, copper, and tin. The antioxidant properties of the anthocyanins can be measured by their capacity to absorb free radicals. The oxygen radical absorbance capacity (ORAC) is a measurement of this. Anthocyanins generally have a high ORAC rating compared to other antioxidants. Further, for ripe berries, there is a linear relationship between ORAC values and anthocyanin content. High ORAC ratings include 25-200 μmole of Trolox equivalents (TE)/g. In most fruits (i.e., not just the fruits with high anthocyanin content), ORAC values ranged from 7.8 to 33.7 μmole TE/g g of fresh berries and the ORAC values of the leaves range from 69.7 to 182.2 μmole TE/g. (Wang S Y, Lin H S., *J Agric Food Chem.* 2000 February; 48(2):140-6). Black raspberries have a very high ORAC of 77 μmole TE/g, while boysenberries have an ORAC of 48 μmole TE/g, and red raspberries and blueberries have 24 and 23 μmole TE/g, respectively. (http://www.deckerfarm.com/antioxidants.html). Acai is another fruit having a high ORAC content. The stage at which the plant is harvested affects the ORAC value. Blackberries have their highest ORAC values during the green stages, whereas red raspberries have their highest ORAC values when ripe. In one embodiment, the antioxidant is selected from a natural product having a high ORAC value. The ORAC may be obtained by using the method described by the U.S. Department of Agriculture's Agricultural Research Service (Prior and Cao, 83(4) J. AOAC INT. 950-6 (2000)). Additionally, testing for ORAC, H-ORAC, N-ORAC, S-ORAC, and ORAC-E (high throughput ORAC for oil-in-water emulsion) are available from Brunswick Laboratories (www.brunswicklabs.com).

Additionally, anthocyanins are collagenase inhibitors. The inhibition of collagenase helps in the prevention and reduction of wrinkles, increase in skin elasticity, etc., which are caused by a reduction in skin collagen.

The anthocyanins useful in the present invention may be obtained from any portion of various plant sources, such as the fruit, flower, stem, leaves, root, bark, or seeds. One of skill in the art will understand that certain portions of the plant may contain higher natural levels of anthocyanins and, therefore, those portions are preferably used to obtain the desired anthocyanins. Methods to determine whether and which portions of a plant contain anthocyanins are known and not discussed herein. The extraction and identification of various anthocyanins are described, for example, in U.S. Pat. No. 6,818,234, U.S. Pat. No. 6,780,442, and U.S. Pat. No. 4,413,004.

Particularly preferred anthocyanins are derived from natural sources having high anthocyanin content. Approximately 300 anthocyanins have been discovered in nature, and come from sources including, but not limited to, acai berries, aronia berries, apples, bilberries, black carrots, blueberries, cherries, cranberries, eggplants, elderberries, grapes, macqui berry, prunes, purple carrots, purple loosestrife, purple rice, radishes, raspberries, red cabbage, redcurrants, red-fleshed potatoes, red raspberries, red onions, species from the *Rubus* class (e.g, black raspberry, blackberry, and youngberry), species from the *Ribus* class (e.g., black currant and gooseberry), sea buckthorn, wolfberry extract, strawberries tart cherry. Two particularly preferred anthocyanins are macquie berry and aronia berry due to their high ORAC. Wild blueberry is another particularly preferred anthocyanin having a high ORAC that may be added to the formulation of the present invention.

Other preferred anthocyanins used in the topical formulation of the present invention are formed from a combination of two or more (i.e., 2, 3, 4, 5, or 6) different sources of anthocyanins. For example, an embodiment may include anthocyanins derived from both aronia berry and from youngberry.

When anthocyanins are used, flavonoid glucuronides and flavonoid glycuronides may be added to the formulation of the current invention as a stabilizer for one or more anthocyanin. As used herein, the term "flavonoid glucuronide" encompasses flavonoids that are attached to a glucuronic acid (e.g., glucose having a carboxylic acid at the C6 position on the sugar ring); the term also encompasses flavonoid glucosides, which are flavonoids attached to glucose. Similarly, flavonoid glycuronides are flavonoids attached to glycuronic acid, and flavonoid glycosides, which are herein encompassed in the term flavonoid glycuronides, are flavonoids attached to a glycose. One particularly useful flavonoid glucuronide is the glucuronide derived from rosemary. Other exemplary flavonoid glucuronides can be found in U.S. Pat. No. 5,908,650.

In one embodiment, an additional antioxidant included in the formulations of the present invention is one or more betacyanin. Betacyanins, like anthocyanins, may be obtained from natural sources and are antioxidants. One betacyanin of interest is betanin found in beets.

A lipoic acid is a preferred antioxidant for use in the topical formulation of the present invention. Lipoic acid is available in both the R and S forms. R-lipoic acid is a preferred form. The lipoic acid of the present invention also includes the reduced form, or dihydrolipoic acid. In aqueous systems, both lipoic acid and DHLA show strong antioxidant activity. Lipoic acid is also useful in treating diseases associated with oxidative stress including liver cirrhosis, atheroschlerosis, and polyneuritis of diabetes mellitus. (Maitra, I., et al., *Free Rad. Biol. Med.* 18:823-829 (1995), introduction). The antioxidative activity of lipoic acid is due, at least in part, to its ability to prevent free radical damage to cells and cell components. Free radical damage is most evident in cellular membranes because of the density of the molecular structure of the membranes. (R)-Lipoic acid has been shown to reverse the age-related decline in oxygen consumption and increase mitochondrial membrane potential. The age-related decline in hepatocellular glutathione and ascorbic acid levels is reversed by treatment with (R)-lipoic acid (as an oral supplement in rats). (Hagen T M, et al., *FASEB J.* 1999 February; 13(2):411-8).

Reduced R-lipoic acid, or R-dihydrolipoic acid (R-DHLA), may be used instead of or in addition to R-lipoic acid. R-DHLA which is formed in situ by the reduction of R-lipoic acid by NADH has more antioxidant properties than lipoic acid. Both DHLA and lipoic acid have metal-chelating capacity (LA chelates $Fe^{2+}$ and $Cu^{2+}$; DHLA chelates $Cd^{2+}$) and can scavenge reactive oxygen species. However, only DHLA can regenerate endogenous antioxidants and repair oxidative damage. DHLA can regenerate the endogenous antioxidants vitamin E, vitamin C and glutathione as well as provide peptide methionine sulfoxide reductase with reducing equivalents. The reducing equivalents help in the repair of oxidatively damaged proteins such as α-1 antiprotease. (Biewenga G P., et al., *Gen Pharmacol.* 1997 September; 29(3): 315-31). DHLA is a potent sulfhydryl reductant and has also been shown to act as a strong direct chain-breaking antioxidant which may enhance the antioxidant potency of other antioxidants such as ascorbate and vitamin E. (Kagan V E, et al., *Biochem Pharmacol.* 1992 Oct. 20; 44(8):1637-49).

Retinol and its derivates such as retinyl palmitate and trans-retinoic acid as well as retinols stabilized in liposomes and cyclodextrin preparations may be added to the present invention. One retinol derivate of interest is tocopheryl-retinoate available from Nikko Chemicals Co. LTD.

Other agents useful in the topical formulation of the present invention include vitamin C and the vitamin C derivatives including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C, such as camu berry (*Myrciaria dubia*), acerola, *emblica officinalis*, and bioflavonoids from rose hip and citrus, may be used including water-soluble bioflavonoids such as hesperidin methyl chalcone. When vitamin C and/or these related easily oxidizable compounds are indicated, the combination with the pyridoxamine and benfotiamine formulation of the present invention is particularly useful for reducing the damaging effects from the potential formation of the oxidation product dehydroascorbate (or related compounds), a species which leads to the formation of AGEs. Therefore, the present invention is particularly useful in combination with topical formulations containing vitamin C.

In one particularly preferred embodiment, the antioxidant is superoxide dismutase (SOD) (and derivatives), catalase (and derivatives), or a mixture thereof. In a particularly advantageous embodiment, SOD is heterologous SOD (HSDs), described in U.S. Pat. No. 6,426,068, which no longer, or practically no longer, exhibit dismutase activity, but which conserve immuno-redox activity, stimulate the production of endogenous SOD, as well as the production of catalase and of glutathione peroxidase. According to another advantageous embodiment includes a plant heterologous SOD that has been derived from melon. Any endogenously occurring form of SOD may be used as the SOD additive in the present invention. The preferred embodiment uses an encapsulated SOD. For example, a formulation of the present invention includes benfotiamine, pyridoxiame, and superoxide dismutase that has been microencapsulated.

Another preferred antioxidant is the mitochondrial-targeted antioxidant tert-butyl hydroxylamine (NtBHA). NtBHA reduces the loss of the mitochondrial enzyme glutamate dehydrogenase (GDH), decreases concentrations of glutathione-mixed disulfides compared to free glutathione. NtBHA is also an inhibitor of AGEs. Proteasomal (organelles within cells that degrade and process proteins through enzymatic reactions) activity was also higher in cells treated with NtBHA than in untreated cells. This is significant since proteasomes break down lipofuscin. The spin trap PBN is believed to hydrolyze to NtBHA, and may be used in combination with the topical NtBHA-containing formulation.

Sesame (*Sesamum indicum*) or sesame lignan may also be added to the present invention. Sesame and its lignans (the fibrous compounds associated with the sesame) act as antioxidants, reduce inflammation, normalize blood pressure, improve lipid levels, and promote fat burning. Sesame has also been shown to aid in protecting and enhancing the bioavailability of fish oil and conjugated linoleic acid, to enhance the anti-inflammatory effects of essential fatty acids, lower total cholesterol and low-density lipoprotein (LDL), block oxidative damage implicated in atherosclerosis, and reduce blood pressure. Sesame lignans can dramatically increase tissue and serum levels of the vitamin E fractions α tocopherol and γ tocopherol, thereby enhancing their protective properties. (Yamashita K, et al., *J Nutr.* 1992; 122(12):2440-6). Studies have shown that sesame can also reduce inflammatory processes known to promote cancer, senescence, and aging.

Sesame seed lignans significantly enhance vitamin E activity and increase α tocopherol concentrations in the blood and tissue of rats fed a diet containing α tocopherol and sesame seed or its lignans. (Yamashita K, et al., *Lipids.* 1995 December; 30(11):1019-28). Additionally, they elevate gamma tocopherol concentration by inhibiting an enzyme involved in breaking down tocopherols and tocotrienols. (Ikeda S, et al., *J Nutr.* 2002 June; 132(5):961-6).

Other preferred antioxidants which may be incorporated in the formulations of the present invention include tocopherols (e.g. d-α-tocopherol, d-β-tocopherol, d-γ-tocopherol, d-δ-tocopherol), tocotrienols (e.g. d-α-tocotrienol, d-β-tocotrienol, d-γ-tocotrienol, d-δ-tocotrienol) and vitamin E (α-tocopherol acetate). These compounds added to the compounds of the present invention may be isolated from natural sources, prepared by synthetic means, or mixtures thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated from, for example, wheat germ oil, grain, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. The increased glutathione peroxidase activity protects the skin from oxidative damage. (Musalmah M, et al., *Asia Pac J Clin Nutr.* 2002; 11 Suppl 7:S448-51). In one particular embodiment the tocopherols and tocotrienols are extracted from Annato.

Gamma tocopherol is one particularly advantageous E vitamin since it is capable of quenching reactive nitrogen oxide species such as peroxynitrite and nitrogen dioxide. (Boje K M. *Front Biosci.* 2004 Feb. 1; 9:763-76). Gamma tocopherol and its water-soluble metabolite, gamma-CEHC, have been shown to reduce inflammation by inhibiting prostaglandin E2 (Jiang Q, et al., *Proc Natl. Acad Sci USA.* 2000 Nov. 10; 97(21):11494-9) and gamma tocopherol administration correlates with a reduced risk from heart disease. (Kushi L H, et al. *N Engl J Med.* 1996 Jun. 2; 334(18):1156-62).

When a tocopherol or tocotrienol is added to the formulation of the present invention, it is also preferable to add sesame oil (or an extract thereof such as sesaminol, a sesame lignans) due to the enhanced antioxidant effect of the combination. (Ghafoorunissa, Hemalatha S., et al., *Mol Cell Biochem.* 2004 July; 262(1-2):195-202; Yamashita K, et al., *Lipids.* 2002 April; 37(4):351-8). One preferred formulation contains d-α-, d-β-, d-γ-, and d-δ-tocopherol, d-α-, d-β-, d-γ-, and d-δ-tocotrienol in addition to the sesame lignans.

Vitamin A is a preferred addition to formulations of the present invention because of the increased stability it can impart to lipoic acids. Segall, A., *J Cosmet Sci.* 2004 September-October; 55(5):449-61.

In addition, carotenoids, particularly the xanthophyll type, are also preferred antioxidants that can be used in the practice of the instant invention. The xanthophyll type carotenoids include molecules such as lutein, canthaxantin, cryptoxanthin, zeaxanthin and astaxanthin. Xanthophylls protect compounds such as vitamin A, vitamin E and other carotenoids (Demmig-Adamas, B. *Biochemica et Biophsyica Acta,* 1020: 1-24 (1990)). Xanthophylls can be obtained from a multitude of natural sources, or produced as described, for example, in U.S. Pat. No. 5,916,791.

Flavan-3-ols are also preferred antioxidants that may be used in the formulations of the present invention; they belong to a class of nutrients known as the flavonoid family. Particularly preferred flavan-3-ols include the procyanidin mixtures extracted from grape (*Vitis vinifera*) seed. Proanthocyanidins play a role in the stabilization of collagen and maintenance of elastin, two critical proteins in connective tissue that support organs, joints, blood vessels, and muscle (Mitcheva et al. *Cell Mol Bio* 39:443-8 (1993) and Maffei et al. *Arzneimittelforschung;* 44:592-601 (1994)). Other flavan-3-ols may also be added to the formulation. These include catechin and epicatechin. Procyanidins are the dimers and oligomers of catechin and epicatechin and their gallic acid esters, and are widely distributed in the plant kingdom and may be added to the formulation of the present invention. Other flavonoids, such as isoflavin β, quercetin, glabridin, red clover, and others described in U.S. Pat. Nos. 5,686,082 and 5,686,367 may also be included in the formulation.

Sunscreen

In particular preferred embodiments, the additional active ingredients included in the compositions of the present invention are compounds having sunscreening action. Sunscreening agents include, but are not limited to, aminobenzoic acid, avobenzone, dioxybenzone, homosalate, lisadimate, menthyl anthranilate, octocrylene, octyl methoxycinnamate, octyl salicylate, oxybenzone, padimate O, phenylbenzimidazole, roxadimate, sulisobenzone, titanium dioxide, trolamine salicylate, zinc oxide, and combinations thereof (see www.nlm.nih.gov/medlineplus/druginfo/uspdi/202782.html). In one particular embodiment the sunscreen agent or agents are naturally occurring substances such as: zinc oxide, coffee oil, leuco-melanin, date palm fruit melanin, galanga extract (available from Symrise). Other substances that protect from UV damage that may be used include such as sanguinaria extract Krameria triandra root extract (15% neolignans) metallothionein, 1,25-dihydroxyvitamin D3, and thymidin dinucleotide. A preferred sun-protective extract is a polypodium leucomotos extract. This compound may be incorporated in the topical formulation, or alternatively, it may be provided as an oral supplement in addition to the formulation of the present invention for increased protection from UV damage. (Middlekamp-hup et al., *J Am Acad Dermatol,* 2004, 51(6) 910-918). One preferred sunscreen agent is isoamyl-p-methoxycinnamate (from Galanga, available from Symrise, Gmbh & Co); this compound provides an spf of greater than 30 using only natural ingredients (botanicals, antioxidants, coffe oil and microfine zinc oxide). Additional sunscreen agents include: allantoin, aloesin, apigenin, caffeic-acid, chlorogenic-acid, ellagic-acid, esculetin, esculin, ferulic-acid, fraxetin, fraxin, lawsone, p-aminobenzoic-acid, paba, procyanidins, rutin, silymarin, squalene, and umbelliferone.

Adding an anti-erythema ingredient to the formula, an additional-effect caused by the damaging UV radiation besides free radical formation is addressed. The reduction in redness accomplished by applying the formulation of the present invention is due to an incorporation of aesculin, colchicines, esculin, glycyrrhetinic-acid, opc, opcs, procyanidin-a-2, procyanidins, rutin, or silymarin into the formulation. Another particularly preferred skin-protective agent is beta glucan, which may be obtained from yeast, oat and mushroom species. It is a free radical scavenger and stimulates nonspecific immunity.

Hyaluronic acid, a component of connective tissue whose function is to cushion and lubricate the tissue as well as hyaluronidase inhibitors such as extracts of *Echinacea* species are also useful as additional agents in the present formulation.

Alpha hydroxy acids, known for their exfoliating and resurfacing properties, may be combined as an ingredient in the topical formulation of the present invention in combination with a saccharide isomerate, green tea, strontium chloride and/or a COX 2 inhibitor to prevent stinging in sensitive individuals.

Hormonal decline is known to occur with aging therefore a class of substances replenishing and regulating these is useful in combination with the formulation of the present invention. A non-exclusive list of agents useful for treating hormonal decline is: estriol, 7-keto-dhea, dhea, estrone, estradiol, progesterone, pregnenolone, melatonin, soy isoflavons, phytoestrogens (back cohosh, red clover, sage etc.) chrysin, diosgenin, vitex extract, diindolmethane, *pueraria mirifica* (puresterol available from bio-botanica), β-sitosterol, β-stigmasterol, betulin and derivatives thereof, *Conyza Canadensis* essential oil, and maca extract standardized to macamides.

Anti-acne agents may also be combined with the formulation of the present invention. Since both free radicals and inflammation are induced by AGEs and are also cofactors in acne, especially in adult skin, a combination with one or more anti-acne ingredient may be used in the topical formulation of the present invention. A non-limiting list of useful anti-acne agents includes: (−)-epigallocatechin, (−)-epigallocatechin-gallate, α-pinene, α-terpineol, anacardic-acid, azelaic-acid, baicalein, berberastine, berberine, β-carotene, camphor, caryophyllene, cryptotanshinone, δ-cadinene, γ-linolenic-acid, indole, linoleic-acid, nerolidol, pufa, pufas, pyridoxine, resorcinol, selenium, sulfur, terpinen-4-ol, thymol, tin, propolis extract and zinc.

Other skin-protective lipids may be used as well; these include ceramides, cerebrosides, essential fatty acids and botanical or marine oils containing these, calophyllum inophyllum squalene, squalane, botanical oils and butters such as (shea butter, meadowsweet oil and coconut oil) phospatidylserine, spingolipids and natural materials containing them such as *Conyza Canadensis*, phospholipids and sulfatet sterols available from Vincience may also be added to protect the skin. Another protective lipid is krill oil rich in omega 3 fatty acids and astaxanthin. This oil is preferably deodorized when used in the topical formulation.

Energizing Ingredients

Energizing ingredients may also be combined with the benfotiamine and pyrodixamine topical formulation. These include the mitochondrial resuscitants and Asian botanicals known to tonify Qi such as *panax* species, *Polygonum multiflorum, Codonopsis silvestris, Astragalus membranaceus, Poria cocos*, or a combination thereof (Chen, J. Zhong Xi Yi Jie He Za Zhi. 1989 April; 9(4):226-7, 198.).

Mitochondrial Resuscitants

Mitochondrial resuscitants may also be added to the benfotiamine and pyridoxamine formulation. Mitochondrial decay in aging is a major driving force behind the aging process. (*Ann N Y Acad Sci.* 2004 June; 1019:406-11; *Proc Natl Acad Sci USA*. 1994 91:10771-8). The mitochondria are the powerhouses of the cell responsible for producing all cellular energy and convert carbohydrates and fatty acids into ATP. ATP is necessary for the production of proteins, which declines with aging (e.g., collagen and elastin). Therefore, the addition of a mitochondrial resuscitant is useful in the present Agents useful as mitochondrial resuscitants include, but are not limited to lipoic acid (Ames B., *Ann. N.Y Acad. Sci.* 1033: 108-116 (2004), carnitine, COQ10, CoA, NADH, FADH, succinic acid, creatine, D-ribose, Sepitonic M3® (containing magnesium aspartate, zinc gluconate, copper gluconate), pyruvate, gymnostemma pentaphyllum, and cytochrome C, adenosine, adenosine monophosphate, adenosine di-phosphate and ATP itself. Additionally, agents including phenylbutylnitrone (PBN) and other spintraps, such as the nitrone or nitroso spin traps described in U.S. Pat. No. 5,723, 502 (N-t-butyl-α-phenylnitrone, 3,5-dibromo-4-nitrosobenzenesulfonic acid, 5,5-dimethyl-1-pyrroline N-oxide, 2-methyl-2-nitrosopropane, nitrosodisulfonic acid, α-(4-pyridyl-1-oxide)-N-t-butylnitrone, 3,3,5,5-tetramethylpyrroline N-oxide, and 2,4,6-tri-t-butylnitrosobenzene) may be used. These agents are antioxidants as well as mitochondrial resuscitants, and therefore have this added benefit when incorporated into the formulation of the present invention.

D-ribose is a naturally occurring five-carbon sugar found in all living cells, and is a preferred mitochondrial resuscitant. It is not an essential nutrient, since it can be made in the body from other substances, such as glucose. However, the application of additional D-ribose can aid in preserving the youthful look of skin. D-ribose, in the form of ribonucleoside diphosphates, is converted to deoxyribonucleoside diphosphates, precursor molecules for DNA. D-ribose in RNA and D-deoxyribose in DNA. When D-ribose is added to the formulation, it is particularly preferred to additionally include an AGE inhibitor to prevent the potential glycating effect of d-ribose.

R-lipoic acid is implicated in mitochondrial energy production and protection from free radicals. It has been shown to maintain microsomal protein thiols, protect against hemolysis, protect against neurological disorders, and protect against ischemia/reperfusion injury. R, not S-lipoic acid is produced by the body and decreases in concentration during the aging process (Pick U., et al., *Biochem Biophys Res Commun*. 1995 Jan. 17; 206(2):724-30). The formulation of the present invention replenishes this vital substance as well as provides protection to the skin cells. R-lipoic acid is incorporated in the formulation in one preferred embodiment of the present invention.

Acetyl-L-carnitine has a three pronged anti-aging effect by being a mitochondrial energy boosting agent, helping to boost acetyl-choline necessary for proper face muscle tone and being an effective antioxidant. It is useful in the transport of long-chain fatty acids into the mitochondrial matrix, transport of short- and medium-chain fatty acids away from the mitochondrial matrix, and regulation of energy metabolism through the modulation of acetyl CoA:CoA ratios. For this regulation, the acetyl group of acetyl CoA is transferred to L-carnitine by carnitine acetyl-transferase (CAT), freeing CoA to participate in the PDH reaction. The acetyl-L-carnitine can then be removed from the mitochondria. (Arrigoni-Martelli E, et al., *Drugs Exp Clin Res*. 2001; 27(1):2749; Rebouche C J. Carnitine. In: Shils M E, et al. eds. *Nutrition in Health and Disease*. 9th ed. Baltimore: Williams & Wilkins; 1999:505-512). This increase of free CoA relative to acetyl CoA, enhances the activity of pyruvate dehydrogenase (PDH) which catalyzes the conversion of pyruvate to acetyl CoA, a crucial reaction in glucose metabolism. (lpi.oregonstate.edu/-infocenter/othernuts/camitine/carnitinerefs.html#ref2)

ATP, adenosine 5'-monophosphate (AMP), and their degradation products may also be administered directly as agents in the topical formulation of the present invention. U.S. Pat. No. 5,227,371 teaches the oral or topical-administration of AMP, ATP or their degradation products adenosine and inorganic phosphate to increase ATP levels. Extracellular ATP has been shown to help regulate vascular tone (Burnstock, G. and Kennedy, *C Circul. Res*. 1986, 58, 319-330), promote muscle contractions (Burnstock, G. *Pharmacol. Rev.* 1972, 24, 509-581), and arresting tumor growth (U.S. Pat. No. 5,049,372). When ATP or other agents susceptible to degradation are used, a stabilized form of the agent is preferred.

Muscle Toning and Enhancing Agents

Cholinesterase Inhibitors and Acetyl-Cholinesterase Inhibitors

Cholinesterase (ChE) and acetyl-cholinesterase inhibitors (AChE) are partially useful as a component in the topical formulation of the present invention because of their ability to augment the restoring of a youthful tone to the face muscles. In one preferred embodiment these ingredients are used on the skin covering a facial muscle that tends to cause facial sagging due to the aging process or the antagonist of a facial muscle that can cause expression wrinkles causing the facial expression muscle to relax. Such method of facial shaping is described with the use of injectable botulinum toxin type A and in this invention these ingredients can be further combined with dermorelaxant ingredients used in the formulation on different skin areas corresponding to the described facial muscles. (Stuzin, J M et al., *Plastic and Reconstructive Surgery* 112(5) Suppl. October 2003 pp 19S-20S).

The ChE inhibitor is preferably obtained from a plant source. Preferred ChE inhibitors include, for example: (+)-carvone, demissine, 1-carvone, solanidine, 1,8-cineole, ephedrine, limonene-oxide, solanine, actinidine, eseramine, lycorine, solasodine, allicin, eseridine, palmatine, thymol, α-chaconine, fenchone, physostigmine, vasicinol, β-2-chaconine, galanthamine, pulegone, bufotenine, huperzine-a, sanguinarine, d-carvone, huperzine-b, selagine, demissidine, ibogaine, and serotonin.

AChE inhibitors are preferably obtained from a plant source. Some preferred AChE inhibitors are: (+)-menthol, berberastine, huperzine-a, menthone, (+)-piperitenone-oxide, berberine, isomenthol, p-cymene, (+)-pulegone, carvone, isomenthone, piperitenone, 1,8-cineole, chelerythrine, isopulegol, pulegone, akuammicine, d-carvone, 1-carvone, sanguinarine, akuammidine, d-limonene, 1-limonene, terpinen-4-ol, alpha-terpinene, elemol, 1-menthol, viridiflorol, (+)-menthol, galanthamine, limonene, yohimbine, (+)-piperitenone-oxide, gamma-terpinene, menthol, and menthone.

Preferably, the ChE or AChE inhibitor is obtained from a plant source. Some preferred ChE or AChE inhibitors are: arecoline, choline, deoxypeganine, deoxyvasicinone, eseridine, galanthamine, iridin, irigenin, lecithin, lithium, nicotine, nobiletin, physostigmine, pilocarpine, pronuciferine, and yohimbine.

Huperzine, an alkaloid derived from the herb *Huperzia Serrata*, is a preferred inhibitor of acetylcholinesterase (AchE) used in the present invention. Huperzine is useful in the forms huperzine A, huperzine B, 6-β-hydroxy huperzine A, and tautomers thereof. Transdermal application of huperzine has been shown to improve memory and cognitive functions by adding huperzine with a permeation enhancer to increase blood plasma levels of huperzine. (U.S. Pub. 2004/020705). Similarly, huperzine can be administered transdermally for the treatment of Alzheimer's disease (U.S. Pat. No. 6,352,715) and cholinergic deficient disorders (WO 2004 080436). In a preferred embodiment, the huperzine-a in the topical formulation is encapsulated in a liposome or nanosome.

Galanthamine is a reversibly acting cholinesterase inhibitor and an acetylcholinesterase inhibitor; it is a tetracyclic alkaloid which was initially isolated from galanthus nivalis. Galanthamine has unique specific properties, for example, highly analgesic effects comparable to those of morphine, and is not as toxic as cholinesterase inhibitors such as physostigmine and neostigmine. The principal use in humans has been the postoperative reversal of neuromuscular blockade. It has also been administered in a number of neuromuscular diseases, and has been shown to enhance activation of motor nerve terminals stimulated electrically, to increase ganglionic depolarization induced by acetylcholine, and to protect against hexamethonium, indicating enhancement of the activity of nicotinic receptors (U.S. Pat. No. 6,670,356). Galanthamine may be isolated, for example, by the process described in U.S. Pat. Nos. 6,617,452 and 6,573,376, from either biological or synthetic material.

Acetyl Choline, Choline, and Precursors

Additional agents are also useful as muscle toning agents. L-α glycerylphosphorylcholine, citicoline (a stabilized CDPCholine (cytidine 5'diphosphocholine), or a stabilized form of citicoline (see U.S. Pat. Nos. 3,687,932 and 6,057,301) may be added. Formulations having these agents are particularly useful when acetyl-1-carnitine is also included in the formulation since the added ingredients enhance the effect of acetyl-1 carnitine and provide the skin with youthful amounts of acetyl choline to prevent sagging and lack of tone to the face.

Alkanolamine such as ethylaminoethanol, methylaminoethanol, dimethylaminoethanol (DMAE), isopropanolamine, triethanolamine, isopropanol-dimethylamine, ethylethanolamine, 2-butanolamine, choline, serine, and mixtures thereof are useful as additional agents in the present invention. They have been shown to be useful for treating wounds. (U.S. Pat. No. 6,319,942). These compounds may increase acetylcholine levels in the skin, by affecting smooth muscle contraction. DMAE is a particularly preferred alkanolamine.

Anti-elastase ingredients are also beneficial as additional ingredients which enhance the formula's ability to firm the skin. These agents include, but are not limited to: PROTEASYL® TP LS 8657 (from Laboratoires Serobiologique), anthocyanins, caffeic-acid, isoquercitrin, procyanidin-a-2, and quercetin.

Molecular film tensors for firming and lifting products may also be used. To help target sagging of skin in addition to tensing agents, ingredients can be included that improve adhesion of cells to the basement membrane and among themselves by enhancing synthesis of laminin V and integrin alpha 6. One such ingredient is Serilesine from Lipotec.

Collagen Enhancing Agents

Collagen enhancing agents such as those described herein may also be added to the present formulation. Agents having 'Collagenic activities' include the anthocyanidins, ascorbic acid, asiatic acid (such as from centella asiatica), aucubin, proanthocyanidins, stabilized vitamin C, the amino acids 1-lysine, 1-proline and their derivatives (e.g., dipalmitoyl-hydroxy-proline, hydroxyproline, homoproline, and natural raw materials containing these such as apt (*Ahnfeltia concinna*) available from CIR)), and copper peptides. Agents having 'Collagenase-Inhibitor activities' include the anthocyanidins, extracts of soy, extracts of apple, eicosapentaenoic acid, proanthocyanidins, procyanidins, bovine cartilage extracts and glycosaminoglycans from shark. Agents having 'Collagen-Sparing activities' include caffeic acid, chlorogenic acid, cichoric acid, cynarin, and echinacoside. Each of these may be used in addition to the lipoic acid, carnitine, and carnosine of the present invention. Alternatively, collagen itself may be added to the formulation such as in the form of collagen peptides (e.g. Active Collagen Polypeptide available from Shanghai UChem Co. LTD.), soluble avian collagen or in a form adapted for delivery to the skin so that the collagen will penetrate into the skin (e.g., the form described in U.S. Pat. No. 6,759,056).

Additional collagen inducing-agents are growth factors, such as EGF, FGF, TGF, TGF-β, HGH (offered in a nanoliposome encapsulation by Regernon, Inc)., NGF, KGF, IGF, natural sources containing growth factors such as colostrums (Pepha® Nutrix from Centerchem), deer antler preparations and peptides designed to increase the production of any of these growth factors (e.g., Syn®-col from Centerchem-TGF-β, Hericium Erinaceus and Idebenone-NGF) or the production of collagen itself (e.g, Matrixyl300, Dermaxyl, and Calmosensine each from Sederma), and collagen peptides. Glucosamine, glucoseamine sulfate, glucosamine HCl, glucosamine ascorbate, chondroitin sulfate and other glucosamine salts and derivatives may be used in the formulation to induce collagen. N-acetyl-glucosamine can be used in one preferred embodiment. Manganese gluconate, a common source of manganese, may also be included in the formulation. The enzyme MnSOD is a powerful antioxidant that removes superoxide radicals.

In one embodiment, a silicon, or an ortho silicic acid described in U.S. Pat. No. 5,922,360 may be used. This ingredient may be used to boost collagen production.

Matrix Metalloproease Inhibitors

Matrix metalloprotease (MMP) inhibitors may also be added to the formulation of the present invention. MMPs are enzymes that play a major role in physiological and pathological destruction of connective tissue, especially collagen. Most MMPs are thiols or hydroxyamates. Many MMPs are neutral zinc-dependent endopeptidases that selectively catalyze the hydrolysis of polypeptide bonds; they degrade and rebuild structural proteins in collagens and are required for the healing of moist skin wounds. (Agren M S. *Arch Dermatol Res*. 1999 November; 291(11):583-90). Increased concentrations of MMP 1 (collagenase 1, interstitial collagenase), 3, (Stromelysin 1), 7 (Matrilysin, PUMP), 9 (Gelatinase B, 92 kD gelatinase), and 12 (Macrophage metalloelastase) have been found in sun-exposed skin. Additionally, increased levels of MMP-1 have been found in smokers. (Lahmann C, et al., Lancet 2001, 357:935-936) MMP levels are also known to rise in fibroblasts as a function of age in both photoaging and natural aging. (Varani J, et al., J Invest Dermatol. 2000 March; 114(3):480-6). Therefore the addition of inhibitors of MMPs, particularly MMP-1, 3, 7, 9, and 11 in the topical formulation of the present invention is contemplated. MMP inhibitors include the tissue inhibitors of metalloproteinases (TIMPs) which are the natural inhibitors of MMP activity (Gomez, D. E. et al. (1997) Eur. J. Cell Biol. 74:111.) and include compounds such as Ilomastat (www.chemicon.com/Product). Other MMP inhibitors useful in the topical formulation of the present invention include those described in U.S. Pat. Pub. 20050058709.

Dermorelaxants

Dermorelaxants, or myo-relaxants that relax the muscles directly beneath the skin, may also be incorporated into the formulation of the present invention. These compounds relax the muscles and reduce wrinkles in the skin. Dermorelaxants include compounds such as myoxinol from cognis, boswellia extract and hexapeptides (available from Lipotech, Spain) and may be incorporated into the formulation of the present invention. Additional dermorelaxants include limonoids such as those described in U.S. Pat. No. 6,866,856. Limonoids are plant alkaloids of the Maliaecae family, such as toosendanin and azadirachtin, are particularly useful for relaxing the facial expression muscles. Additional myo-relaxant ingredients also include alverine and its salts (e.g., alverine citrate), sapogenins (e.g., diosgenin or diosgenin extract from wild yam), salts of manganese (e.g., manganese gluconate), adenosine, the hexapeptide argireline R (LIPOTEC), and Syn®-Ake, a a synthetic tripeptide that mimics the effect of Waglerin 1, a peptide that is found in the venom of the Temple Viper, Tropidolaemus wagleri. See as described in U.S. Pat. No. 6,866,856. Additional dermorelaxants include Boswelox™ which is a combination of boswellia serrata extract and manganese (LOreal). In one preferred embodiment the dermorelaxant ingredient(s) are used on the skin covering expression muscles or on the antagonist of a facial muscle that tends to cause facial sagging due to the aging process. Such method of facial shaping is described with the use of injectable botulinum toxin type a. (Stuzin, J M, *Plastic and Reconstructive Surgery* 112(5) Suppl. October. 2003 pp 19S-20S).

Other agents useful for relaxing the skin that may be added to the present formulation include 3-o-acetyl-11-ketoboswellic acid or plant extracts containing this compound (U.S. Pat. Pub 2004/0166178, herein incorporated by reference).

Anti-Inflammatory Agents

The free radicals associated with aging skin will often also induce inflammation in the skin and lack of skin immunity. Therefore anti-inflammatory agents including NSAIDS, COX-2 inhibitors (e.g., nexrutine, ursolic acid, quercetin, curcumine, and evodia extract. (Kang, S. S., et al., Nat. Prod. Sci., 1999, 5(2): 65-69.) can be included in the formulation of the present invention. Ingredients for sensitive skin including endorphin modulating ingredients and anti-irritants can also be added to the formula. Such one example is described in WO 98/07744 and U.S. Pat. No. 6,272,717

In one preferred embodiment, the formulation comprises benfotiamine, pyridoxamine, pyruvate, biotin, and a COX-2 inhibitor. This embodiment is particularly useful because of the combined properties afforded by these agents. The pyruvate has a dual function of AHA-like exfoliation and ATP-enhancement. Through co-carboxylase (from benfotiamne) and carboxylase (biotin), the pyruvate will convert to Co-A. Benfotiamine is both an AGE inhibitor and a Co-A facilitator. The COX-2 inhibitor is added to minimize any potential stinging from the pyruvic acid or other AHA that may be included.

Other Agents

An additional antioxidant that may be used in the present invention is a phenylpropanoid glycosides. Martynoside, a particularly preferred phenylpropanoid glycoside, may be isolated from a number of botanical sources such as: *Clerodendron trichotomum* (apps1.niaid.nih.gov/struct_search/); the aerial section of *Scutellaria pontica*. (Ersoz T, et al., Turkish J. Chem. "Phenolic Compounds from *Scutellaria pontica*", which also provides the isolation of other phenylalkyloid glycosides); transformed root cultures of *Catalpa ovata* (Halina Wysokinska J, et al., *Free Radic Res.* 2003 August; 37(8):829-33); *Pedicularis plicata* (Liao R et al., *Phytotherapy Research* 1999 13(7):621-623; which also provides the isolation of verbascoside); *Pedicularis* (Wang et al., *Sci China C Life Sci* (1996) 39(2):154-8; which also provides the isolation of the phenylpropanoid glycosides: echinacoside, verbascoside, leucosceptoside A, and pediculariosides A, M and N). Their antioxidant scavenging activities are similar to those of the o-dihydroxy group of phenylpropanoid glycosides (Wang et al., *Biochem Pharmacol* (1996) 51(5): 687-91). The addition of martynoside or verbascoside as an ingredient in the formulation of the current invention is particularly advantageous because these phenylpropanoid glycosides have been shown to reduce fatigue in muscle tissue. This allows for a relaxation and smoothing in the overlying skin and reduces the signs of aging. (Liao R et al., *Phytotherapy Research* 1999 13(7):621-623).

Depigmenting agents may be added as an additional agent in the present invention. Depigmenting agents include tyrosinase inhibitors such hydroquinone and its derivatives (e.g., hydroquinone monomethyl ether, hydroquinone monoethyl ether, arbutin), soy and derivatives thereof, retinoids such as retinol; Kojic acid and its derivatives (e.g., kojic dipalmitate); transexamic acid; vitamins such as niacin, vitamin C and its derivatives; azelaic acid; phytic acid, licorice; mulberry extracts; extracts from *rumex* species such as *rumex crispus* extract; chamomile extracts; green tea extracts; lactic acid, pearl extract, *Tricholoma matsutake* extract, magnesium-asorbyl-phosphate, edelweiss extract, sedum acre extract, arbutine, ergothione, *phyllantus emblica* extract, α-MSH antagonists such as Undecylenoyl phenylalanine, *germanium*, and GABA and songyi mushroom. Bowman-Birk Inhibitors are described in U.S. Pat. No. 6,750,229 (e.g., inhibitors derived from the leguminosae, solanaceae, gramineae or cucurbitaceae family). Dermalight® and Clariskin3® from Silab are also depigmenting agents that can be used. Kinetin (N6 furfuryladenine) is a 6-(R-amino)purine cytokinin and is described in U.S. Pat. Nos. 5,602,139, 5,164, 394, and 5,021,422. It has been shown to have anti-aging effects on the skin of dogs as well as the depigmenting effects without adverse effects. (Kimura T, Doi K., *Rejuvenation Res.* 2004 Spring; 7(1):32-9).

Compounds having "anticapillary-fragility" activity may also be included as an additional ingredient. Capillary fragility can cause telangiectasia and spider veins. Furthermore, AGES and free radicals can cause damage to the fine vessels and induce telangiectasia or spider veins; therefore this class of agents is also useful to augment the benfotiamine and pyridoxamine formulation. These agents include, but are not limited to: aescin, aesculetin, aesculetol, aesculin, aesculoside, diosmin, escin, esculetin, esculin, hederagenin, hesperidin, hydroxyethylrutoside, hyperoside, inulicin, luteolol, maniflavone, neoruscogenin, patulin, procyanidin-a-2, quercetol, quercetoside, rhamnetol, ruscogenin, rutin, rutoside, and xanthorhamnoside. Additionally, microcirculation decreases with age, especially around the eyes. Therefore this class is also beneficial and includes hydroxysuccinimide, chrysin (and other bilirubinolytic substances such as gardenin, gardenoside, berberine) or ingredients containing such substances eg Haloxyl from Sederma, Nattokinase, and vitamin K in its forms, including menaquinone-7.

In a preferred embodiment, liposomes made by the process described by AGI Dermatics (New York) may be used. These photosomes and ultrasomes are be useful in formulations used to target DNA repair associated with photoaging and are described in U.S. Pat. Nos. 6,623,724 and 6,479,533. A marine-derived photolyase, a DNA-repair enzyme from Anacystis nidulans plankton may be added to the formulation. These enzymes, incorporated into a liposome (e.g., Photosome®) are adsorbed through the skin and repair sun-damaged DNA. Redness and sunburn cell formation may also be reduced or prevented by the addition of these enzymes.

Ethylenediaminetetraacetate (EDTA) or other metal chelators are preferred antioxidants that can be included in the compositions. Plant tannins are also metal chelators that may also be included in the composition. The chelating agent forms a complex with metal ions, inactivating them, and preventing them from affecting antioxidant activity. Other chelators include, but are not limited to dihydroxyethyl glycine, citric acid, tartaric acid, and mixtures thereof.

Glutathione, reduced glutathione, glutathione peroxidase, glutathione s-transferase or glutathione reductase may be incorporated in the formulation of the present invention. Additionally, synergistic intracellular glutathione inducers and precursors of glutathione may be used. These include ornithine, α-ketoglutarate, 1-cystein, 1-glycine, 1-glutamatic acid, glycyl-1-glutamine, n-acetyl-cystein, riboflavin, vitamin B6, parsley seed or seed extract, sylimarin, and cysteine whey peptides.

Aldenine, which comprises a vegetal protein hydrolysate and a synthetic tripeptide, may be included in the formulation of the present invention. Aldenine is able to boost Collagen III production.

Centrophenoxine (Lucidril®) is another agent that may be added to the pyridoxamine and benfotiamine formulation. It contains both dimethylaminoethanol (DMAE) and p-chlorophenoxyacetate. DMAE is found in food and is also a metabolite. pCPA is a synthetic compound related to plant hormones known as auxins. Centrophenoxine has been shown to remove lipofuscin, a cellular residue that accumulates over the life of the cell. Additionally, it has been shown to have an effect as a cognition enhancer. (J. Am. Geriatr. Soc. (USA), 1978, 26:2, 74-81.)

In one embodiment, the topical benfotiamine and pyridoxamine formulation is taken in conjunction with an oral supplement containing one or more anti-glycation agent. The added benefit of an oral supplement containing one or more anti-glycation agent has been demonstrated, for example, by Thirunavukkarasu V, et al., who demonstrated that oral consumption of α-lipoic acid affects the content and characteristics of the protein collagen from skin of high-fructose fed rats. (*Exp Diabesity Res.* 2004 October-December; 5(4):237-44.) Any AGE inhibitor suitable for oral consumption may be administered. One particularly preferred oral AGE inhibitor is carnosine. In one example, the oral supplement comprises a capsule containing 50-150 mg benfotiamine, 50-500 mg 1-carnosine, 25-150 mg pyridoxamine and 25-150 mg lipoic acid.

The ingredients included in the oral formulation may also be nutrients for hair, skin and nails (including, for example, stabilized orthosilicic acid, biotin, hyaluronic acid and essential fatty acids available from plant, animal and marine sources. Examples of these fatty acids include lipids such as fish oil and krill oil. Other ingredients include weight loss encouraging agents (e.g., carbogen (from Triarco), *hoodia gordonii* extract, *coleus forskholii* extract, CLA, 7-Beta-Hydroxy-DHEA, carnitine, cholecystokinin releasing agents such as Satise (from Kemin) cognition enhancing agents (acetyl-1-carnitine, citicholine, huperzine, DMAE, *Bacopa Monneiri* extract, Sage extract, L-alpha Glyceryl Phosphoryl Choline, Ginko Biloba, Vinpocetine, DHA, nootropics including Phenyltropin, Pikatropin (from Creative Compounds). Other agents include sleep and mood enhancing ingredients (e.g., melatonin, S-AME, GABA), probiotics, stabilized probiotics such as Probiocap (Institute Rosell), antioxidants, energizing ingredients, libido enhancing ingredients, wellness enhancing ingredients and multivitamin and mineral combinations. The use of the benfotiamine and pyridoxamine in conjunction with the oral formulation eliminates or decreases the potential glycation effects of these substances (such as ascorbate and D-ribose or Pufas), allowing these nutrients to open their full beneficial potential. These oral agents may be used, as appropriate (i.e., they must adsorb through the skin) in the topical formulation as well. Alternatively, topical agents as described hereinabove that have glycating effects may be taken orally, as appropriate nutraceuticals.

The additional agent can be used as the sole additional active agent in the pyridoxamine and benfotiamine topical formulation. They also may be used in combination with 1, 2, 3, 4, 5, 6, 7, 8, 9, 10, 11, 12, or more other agents. The amount of additional agent in the preparation, alone or in combination, is preferably from about 0.00 to about 30% by weight, preferably from about 0.1 to about 5% by weight, based on the total weight of the preparation.

V Topical Formulations

The formulations of the present invention may also comprise pharmaceutically acceptable topical auxiliaries. Pharmaceutically acceptable auxiliaries are those which, as is known, can be used in the field of pharmacy, food technology and related fields, in particular, those listed in relevant pharmacopeia (e.g. DAB Ph. Eur. BP NF), and other auxiliaries whose properties do not impede physiological use.

Suitable carriers include water, alcohols, oils and the like, chosen for their ability to dissolve or disperse the active ingredients at concentrations of active ingredients most suitable for use in the therapeutic treatment. Generally, even low concentrations of active ingredients in the carrier will be suitable, requiring only the more frequent application of the topical composition. The present invention provides that the topically applied composition be formulated to contain at least about 0.001% up to about 80% by weight, more preferably from about 0.01% to about 20% by weight, and even more preferably from about 0.1% to about 5% by weight, of a benfotiamine and at least about 0.001% up to about 80% by weight, more preferably from about 0.01% to about 20% by weight, and even more preferably from about 0.1% to about 5% by weight of a pyridoxamine and, accordingly, carriers can be chosen which will solubilize or disperse the active ingredients at such concentrations. One particularly efficacious embodiment contains about 2% by weight of a benfotiamine and 3% by weight of a pyridoxamine in a liposomal carrier. In another embodiment, the topically applied composition is formulated to contain at least about 0.001% up to about 0.05% by weight, more preferably from about 0.01% to about 0.05% by weight, of a benfotiamine and at least about 0.001% up to about 80% by weight, more preferably from about 0.01% to about 20% by weight, and even more preferably from about 0.1% to about 5% by weight of a pyridoxamine and a carrier.

Suitable auxiliaries may be lubricants, wetting agents, emulsifying and suspending agents, preservatives, anti-irritants, emulsion stabilizers, film formers, gel formers, odor masking agents, resins, hydrocolloids, solvents, solubilizers, neutralizing agents, permeation accelerators, pigments, quaternary ammonium compounds, refatting and superfatting agents, ointment, cream or oil base materials, silicone derivatives, stabilizers, sterilizing agents, propellants, drying agents, opacifiers, thickeners, waxes, emollients, or white oils.

According to the invention, the formulations are administered topically, to the area of skin that is to be treated. The topical administration provides the AGE-inhibiting formulation to the skin. The composition is administered in a subject susceptible to or having an accumulation of AGE, preferably a human being. It may be administered according to a dosage and administration regimen defined by routine testing.

In one embodiment, the topical benfotiamine and pyridoxamine formulation is combined with iontophoresis to enhance permeation. In particular, iontophoresis using less than 1000 µA, or more particularly less than 600 µA. In addition, this method of administering the topical formulation may be combined with additional oral pyridoxamine and benfotiamine supplement, which is particularly contemplated for use by diabetic patients or where AGEs/ALEs inhibition is particularly important for treating the skin, and where other uses for AGE/ALE inhibiting may be warranted.

The area to which the formulation of the present invention is applied may be determined based on the type of muscles underlying the skin. For example, the pyridoxamine and benfotiamine formulation containing a dermorelaxant may be preferably applied to skin that covers expression muscles. Expression muscles include facial muscles (belly and muscle attachments). Alternatively, a formulations including ingredients that have muscle toning properties (AChE inhibitors, ChE inhibitors, anti-elastase properties and/or molecular film tensors), the formulation is preferably applied to skin areas covering muscles known to sag and loose their tone due to the aging process. In one embodiment, a formulation including a dermorelaxant is applied to one part of the face while a different formulation containing a toning agent is applied to another part of the face, dependent upon the underlying muscles.

While the carrier for the combination of benfotiamine and pyridoxamine can consist of a relatively simple solvent or dispersant such as an oil, it is generally preferred that the carrier comprise a composition more conducive to topical application, and particularly one which will form a film or layer on the skin to which it is applied so as to localize the application and provide some resistance to perspiration, and/or one which aids in percutaneous delivery and penetration of the active ingredients into lipid layers. Many such compositions are known in the art, and can take the form of creams, gels, ointments, hydrogels, pastes or plasters, and liquid dosage forms, such as solutions, emulsions, in particular oil-in-water emulsions, suspensions, (for example, lotions, etc), or even solid sticks. If desired, it is also possible to use liposomes or microspheres.

To prepare the dermatological compositions according to the invention, the active ingredients can be mixed or diluted with a suitable auxiliary (excipient). Excipients can be solid, semisolid or liquid material which may serve as vehicle or carrier medium for the active ingredient. The other auxiliaries, if desired, are mixed in the manner known to the person skilled in the art.

If desired, two or more active ingredients can be formulated together. They can, however, also be initially processed separately and then combined in a suitable dosage form.

In one aspect of the present invention, the benfotiamine and pyridoxamine formulation is stabilized using microencapsulation. Microencapsulation can protect the active agents from the surrounding environment and increase the effectiveness as an anti-aging agent since more agents will remain active as the skin layer has been penetrated. Processes conventionally used for microencapsulation may be employed, and may comprise encapsulation by nanosomes, liposomes, or other vehicles known in the art.

The microcapsules may be prepared, for example, by coacervation techniques or by interfacial polymerization, for example, hydroxymethylcellulose or gelatin-microcapsules and poly(methylmethacrylate) microcapsules, respectively, in colloidal drug delivery systems (for example, liposomes, albumin microspheres, microemulsions, nanoparticles and nanocapsules) or in macroemulsions. (Remington's Pharmaceutical Sciences (A. Osol ed., 16th ed. (1980)). Microencapsulation is particularly useful for formulations containing DHLA, which is prone to degradation and oxidation.

One typical process is to dissolve the shell material in a solvent (in the form of a colloidal or true solution) and to disperse the core material in the resulting solution in the form of solids or microdroplets. This dispersion is divided into microdroplets and then heated using, for example, hot air. During this process, the solvent evaporates and the shell material re-precipitates in the form of solids and forms a shell around the core material. This gives crude microcapsules, which can then be subjected to the customary processing steps and incorporated into the final formulations. This process utilizes the known phenomenon of coacervation.

Another process of microencapsulation uses interface polymerization to create the microcapsule shell. In this method, precursors of the shell material, for example monomers, are concentrated onto the core material, where they polymerize to give the final shell film. Fat-coating processes also may be used.

The materials used for microencapsulation are selected from conventional hydrophilic or hydrophobic substances or mixtures thereof. Solids, in particular natural polymers, for example, starch and other polysaccharides, are preferred. However, synthetic polymers can also be used. Examples of shell materials are fats and/or waxes, preferably those having a solidification temperature of approximately 35°-80° C. and include mixtures of cetyl palmitate and cetyl alcohol. Other compounds include polysaccharides and their derivatives of natural or partially synthetic origin, (e.g. cellulose derivatives); further, polymers of α- and/or β-hydroxycarboxylic acids, in particular polymers of glycolic acid (polyglycolides), lactic acid (polylactides), α-hydroxybutyric acid (polyhydroxybutyrate), α-hydroxyvaleric acid (polyhydroxyvalerate) and/or their copolymers, or mixtures of such polymers and/or copolymers.

Independently of the specific technique for preparing the microcapsules, it is preferred to carry out the process at a temperature which does not cause any of the components of the formulation to decompose or lose their antioxidant activity.

Similarly, nanoencapsulation may be used. Nanoemulsions are metastable oil-in-water emulsions having a globule size is less than 150 nm. They can be stabilized with amphiphilic lipids Nanoemulsions are structurally distinct from microemulsions which are thermodynamically stable dispersions comprising micelles of at least one amphiphilic lipid swollen with oil and do not require mechanical energy to be prepared. An advantage of using nanoencapsulation is the reduced need for surfactants, which may tend to lead to intolerance and entailing a sticky feel when applied to the skin. (See U.S. Pat. No. 6,562,356).

In one embodiment, the formulation is encapsulated in cyclodextrine. Such process is performed, for instance, by the Wacker group.

In another embodiment, the formulation is encapsulated with NADH, R-DHLA, ATP, Glutathione and SOD in Nano Spheres. Such process is performed, for instance, by Salvona Technologies. In another embodiment, biopolymer nanoemulsions from Ivrea-Pak Tech are used to eliminate undesirable residue ("ghosting") commonly associated with porous particulate entrapment formulations.

One particular embodiment comprises the use of novel dispersions of hydrophobes to yield a surfactant-free formulation, by subjecting the materials to high pressure, high shear processing. Cold process formulations are also a preferred method as they protect certain heat-sensitive agents in the formulation; they can be obtained by using self-emulsifying oleosomes such as Natrulon OSF available from Lonza. In one embodiment, the formulation is processed using the carriers and dry-water process of Aerosil® (Degussa), which is based on fumed silica or in a liquid formulation trademarked AERODISP. (See www1.sivento.com/wps3/portal/en/aerosil/industries/personal0.htm1).

According to the invention, the formulations are administered topically in the form of a cream, gel, or liquid. The topical administration provides the benfotiamine and pyridoxamine-containing formulation directly to the skin, which is preferably provided with the use of a dermatologically acceptable carrier. While the carrier may consist of a relatively simple solvent or dispersant, such as an oil, it is generally preferred that the carrier comprise a material more conducive to topical application, and particularly one which will form a film or layer on the skin to which it is applied. This localizes the application and provides some resistance to perspiration and/or aids in percutaneous delivery and penetration of the active ingredients into lipid layers. Many such compositions are known in the art, and can take the form of creams, gels, ointments, hydrogels, pastes or plasters, and liquid dosage forms, such as solutions, emulsions, in particular oil-in-water emulsions, suspensions, for example lotions, etc., or even solid sticks. Liposomes or microspheres may also be used.

In some embodiments, the topical formulation will be administered using a device or method designed to more readily break the skin barrier and provide the agents in the topical formulation with a faster or more effective means through the stratum corneum. This nanosomal delivery includes, for example, oxygen nebulizers and nanosomal mist in conjunction with iontophoresis. A spray or nebulizer may be used to create the nanosomal mist. In one embodiment, the micro-electronic cosmetic delivery mechanism described as PowerCosmetics™ may be used for delivery of the topical agent to the skin. This method is useful for delivering ionizable compounds to the skin and aids the penetration of small molecules through the stratum corneum. (www.powerpaper.com).

The method of the present invention is particularly useful for the prevention of skin damage which may result from the formation of AGEs.

Generally, the composition is topically applied to the affected skin areas in a predetermined or as-needed regimen to bring about improvement, it generally being the case that gradual improvement is noted with each successive application. The presence of AGEs in the skin can be determined by a relatively simple test. Since several AGEs exhibit fluorescence, a noninvasive autofluorescence reader can be used to measure the relative concentration of these fluorescent AGEs in the skin. Therefore, the effectiveness of the AGE-inhibition properties of the topical formulation of the present invention may be measured. (Meerwaldt, R., et al., *Ann N Y Acad Sci.* 2005, 1043:290-8; Meerwaldt, R., et al., *Ann N Y Acad Sci.* 2005, 1043:911). Particularly, the concentration of AGEs in a certain location of the skin can be measured by fluorescence spectroscopy before treatment with the formulation of the present invention. After treatment, the fluorescence is measured again and compared to the first measurement. The formulation may inhibit the formation of AGEs by reducing the AGE concentration by at least 20%, or more particularly 30%, 40%, or even more particularly 50%. In one measurement regimen, the second measurement occurs after four or more weeks of treatment, where treatment refers to topical application at least once daily.

Each reference cited herein is hereby incorporated by reference in its entirety.

EXAMPLES OF TOPICAL COSMETIC PREPARATIONS OF THE INVENTION

The following Examples are provided to illustrate the invention without being limiting in any way.

Example 1

| Ingredient | % by weight |
|---|---|
| pyridoxamine | 3.00 |
| benfotiamine | 2.00 |
| carnosine | 1.00 |
| astaxanthin | 1.00 |
| tocotrienols | 0.50 |
| tocopherols | 0.50 |
| grape proanthocyanidins | 0.50 |
| E.D.T.A. (ethylenediamine tetracetic acid) | 0.05 |

Example 2

| Ingredient | % by weight |
|---|---|
| pyridoxamine | 0.5 |
| benfotiamine | 0.2 |
| billberry anthocyanins | 1.0 |
| shark derived glycosaminoglycans | 1.0 |
| green tea polyphenols | 2.0 |
| tocopherols | 0.5 |
| α G-rutin* | 1.0 |

*α-G-rutin can be obtained from Toyo Sugar Refining Co., LTD. Japan.

Example 3

| Ingredient | % by weight |
|---|---|
| Pyridoxamine | 1.0 |
| Benfotiamine | 1.0 |
| Lutein | 0.5 |

-continued

| Ingredient | % by weight |
| --- | --- |
| Tetrahexyldecylascorbate | 3.0 |
| Lycopene | 0.5 |
| coenzyme Q10 (ubiquinone) | 0.1 |
| Curcumine | 0.5 |

Example 4

| Ingredient | % by weight |
| --- | --- |
| Pyridoxamine | 3.0 |
| Benfotiamine | 3.0 |
| Carnosine | 3.0 |
| Carnosol | 0.01 |
| aminoguanidine | 0.1 |
| Tocotrienols | 0.1 |
| Tocopherols | 0.5 |
| retynyl palmitate | 0.5 |
| tetrahydrocurcuminoids (a curcumin derivative) | 1.0 |

Example 5

| Ingredient | % by weight |
| --- | --- |
| pyridoxamine | 1.0 |
| benfotiamine | 1.0 |
| pyridoxanine | 1.0 |
| pyridoxal 5'-phosphate | 1.0 |
| pyridoxamine 5'-phosphate | 1.0 |
| thiamine | 1.0 |

Example 6

| Ingredient | % by weight |
| --- | --- |
| pyridoxamine | 1.0 |
| benfotiamine | 1.0 |
| pyruvate | 1.0 |
| biotin | 1.0 |
| quercetin | 1.0 |

This particular formulation is useful for the combination of the benfotiamine and pyridoxamine as discussed above with pyruvate providing exfoliation and ATP-enhancing activity. Additionally, through cocarboxylase (from benfotiamine) and carboxylase (biotin) the pyruvate would be converted to Co-A and provide additional anti-aging activity. The quercetin is added to minimize any potential stinging from pyruvic or other aha that may be included.

Having described the invention with reference to particular compositions, it will be apparent to those skilled in the art that it is not intended that the invention be limited by such illustrative embodiments, and that the modifications can be made without departing from the scope or spirit of the invention, as defined by the appended claims. It is intended that all modifications and variations be included with the scope of the invention.

What is claimed is:

1. A topical dermatological formulation selected from the group consisting of a composition having the active components:
   3% Pyridoxamine,
   2% Benfotiamine,
   1% Carnosine,
   1% Astaxanthin,
   0.5% Tocotrienol,
   0.5% Tocopherol,
   0.5% grape proanthocyanidin, and
   0.05% ethylenediamine tetracetic acid;
a composition having the active components:
   0.5% Pyridoxamine,
   0.2% Benfotiamine,
   1% billberry anthocyanin,
   1% shark derived glycosaminoglycan,
   2% green tea polyphenol,
   0.5% tocopherol, and
   1% α G-rutin,
a composition having the active components:
   1% Pyridoxamine,
   1% Benfotiamine,
   0.5% Lutein,
   3% Tetrahexyldecylascorbate,
   0.5% Lycopene,
   0.1% coenzyme Q10, and
   0.5% Curcumine,
a composition having the active components:
   3% Pyridoxamine,
   3% Benfotiamine,
   3% Carnosine,
   0.01% Carnosol,
   0.1% Aminoguanidine,
   0.1% Tocotrienol,
   0.5% Tocopherol,
   0.5% retynyl palmitate, and
   1% tetrahydrocurcuminoid,
a composition having the active components:
   1% Pyridoxamine,
   1% Benfotiamine,
   1% Pyridoxanine,
   1% pyridoxal 5'-phosphate,
   1% pyridoxamine 5'-phosphate, and
   1% thiamine, and
a composition having the active components:
   1% Pyridoxamine,
   1% Benfotiamine,
   1% Pyruvate,
   1% Biotin, and
   1% Quercetin.

2. The topical dermatological formulation of claim 1, having the active components:
   3% Pyridoxamine,
   2% Benfotiamine,
   1% Carnosine,
   1% Astaxanthin,
   0.5% Tocotrienol,
   0.5% Tocopherol,
   0.5% grape proanthocyanidin, and
   0.05% ethylenediamine tetracetic acid.

3. The topical dermatological formulation of claim 1, having the active components:
   0.5% Pyridoxamine,
   0.2% Benfotiamine,
   1% billberry anthocyanin, 1% shark derived glycosaminoglycan,
2% green tea polyphenol,
0.5% tocopherol, and
1% α G-rutin.

4. The topical dermatological formulation of claim 1, having the active components:
1% Pyridoxamine,
1% Benfotiamine,
0.5% Lutein,
3% Tetrahexyldecylascorbate,
0.5% Lycopene,
0.1% coenzyme Q10, and
0.5% Curcumine.

5. The topical dermatological formulation of claim 1, having the active components:
3% Pyridoxamine,
3% Benfotiamine,
3% Carnosine,
0.01% Carnosol,
0.1% Aminoguanidine,
0.1% Tocotrienol,
0.5% Tocopherol,
0.5% retynyl palmitate, and
1% tetrahydrocurcuminoid.

6. The topical dermatological formulation of claim 1, having the active components:
1% Pyridoxamine,
1% Benfotiamine,
1% Pyridoxanine,
1% pyridoxal 5'-phosphate,
1% pyridoxamine 5'-phosphate, and
1% thiamine.

7. The topical dermatological formulation of claim 1, having the active components:
1% Pyridoxamine,
1% Benfotiamine,
1% Pyruvate,
1% Biotin, and
1% Quercetin.

8. The topical dermatological formulation of claim 1, wherein the formulation is placed in a container, said container being airtight, the container substantially blocks light between 450 and 720 nm, or a combination thereof.

9. The topical dermatological formulation of claim 1, wherein the components are encapsulated in liposomes or nanosomes.

10. A method of inhibiting the formation of advanced glycation endproducts (AGEs) in the skin, said method comprising topically applying to skin areas to be treated a composition according to claim 1.

11. The method of claim 10, further comprising orally administering an AGE inhibitor.

12. The method of claim 10, wherein inhibition of the formation of advanced glycation endproducts occurs after or concurrently with the oral ingestion or topical application of a sugar, amino acid, or vitamin C derivative, wherein the sugar, amino acid, or vitamin C derivative is either prone to glycation or has an oxidation product that is prone to glycation.

13. The method of claim 10, wherein the composition is in the form of a makeup product.

14. The method of claim 10, wherein inhibiting the formation of advanced glycation endproducts comprises reducing the advanced glycation endproduct formation in the skin by at least 50%.

15. The method of claim 10, further comprising inhibiting the formation of advanced lipoxidation end products.

\* \* \* \* \*